United States Patent
Srinivasan et al.

(10) Patent No.: US 8,895,778 B2
(45) Date of Patent: Nov. 25, 2014

(54) DEPOLYMERIZATION OF POLYLACTIC ACID

(75) Inventors: Gowrishankar Srinivasan, Ames, IA (US); David Grewell, Ames, IA (US)

(73) Assignee: Iowa State University Research Foundation, Ames, IA (US)

( * ) Notice: Subject to any disclaimer, the term of this patent is extended or adjusted under 35 U.S.C. 154(b) by 138 days.

(21) Appl. No.: 13/357,442

(22) Filed: Jan. 24, 2012

(65) Prior Publication Data

US 2013/0096342 A1  Apr. 18, 2013

Related U.S. Application Data

(60) Provisional application No. 61/546,891, filed on Oct. 13, 2011.

(51) Int. Cl.
*C07C 51/42* (2006.01)
*C07C 51/41* (2006.01)
*C07C 51/09* (2006.01)

(52) U.S. Cl.
CPC .............. *C07C 51/09* (2013.01); *C07C 51/412* (2013.01)
USPC .......................................... 562/589; 562/593

(58) Field of Classification Search
USPC .................................. 562/589, 593
See application file for complete search history.

(56) References Cited

PUBLICATIONS

Motoyama et al, Polymer Degradation and Stability (2007), 92(7), pp. 1350-1358.*
Translation of JP08-253619 A, to Matsushita et al, published 1996.*
Sanchez, A.C.; Collinson, S.R. The selective recycling of mixed plastic waste of polylactic acid and polyethylene terephthalate by control of process conditions. European Polymer Journal 2011, 47, pp. 1970-1976.
Tsuneizumi, Y., et al. Chemical recycling of poly(lactic acid)-based polymer blends using environmentally benign catalysts. Polymer Degradation and Stability 2010, 95, pp. 1387-1393.

* cited by examiner

*Primary Examiner* — Kamal Saeed
*Assistant Examiner* — Janet L Coppins
(74) *Attorney, Agent, or Firm* — Haukaas Fish PLLC; Michael H. Haukaas

(57) ABSTRACT

The invention provides energy efficient depolymerization of polyesters such as post-consumer polylactic acid. Ultrasonic induced implosions can be used to facilitate the depolymerization. The expanding market of polylactic acid-based plastic products, such as water bottles and packaging materials, has raised concerns of contaminating the recycling stream, which is largely filled with petroleum-based plastics. Thus the development of an energy efficient and economically viable PLA recycling process is urgently needed. Post consumer PLA was exposed to methanol as the suspension media in the presence of organic or ionic salts of alkali metals such a potassium carbonate and sodium hydroxide as depolymerization catalysts to provide high quality lactic acid monomers in high yield.

21 Claims, 26 Drawing Sheets

DEPOLYMERIZATION OF POLYLACTIC ACID

RELATED APPLICATIONS

This application claims priority under 35 U.S.C. §119(e) to U.S. Provisional Patent Application No. 61/546,891, filed Oct. 13, 2011, which is incorporated herein by reference.

GOVERNMENT SUPPORT

This invention was made with government support under Grant No. DA13-09BIO-003 awarded by the United States Department of Agriculture. The United States Government has certain rights in the invention.

BACKGROUND OF THE INVENTION

In terms of environmental pollution, the adverse effects of petroleum plastics has lead to increased use of bio-renewable and degradable bio-polyesters such as polylactic acid (PLA) and poly-hydroxyl butyrate (PHB). PLA has become a widely accepted resin in the plastics and packaging industries. The growing supply of PLA has enabled companies such as Nature Works, Naturally Iowa, and PepsiCo to manufacture and use "eco-friendly" water bottles and food packaging products. This growth is largely due to strong marketing of PLA's claimed environmental benefits and the reduced cost of PLA resin, which is now comparable to that of conventional polymers such as polyethylene. Despite being bio-renewable and biodegradable, the processability and mechanical properties of PLA have been major hurdles in the way of achieving widespread acceptance by industry. Concern regarding contamination of conventional plastic recycling streams has also resurfaced. These issues drive the need to develop a recycling method that would both improve the long-term viability of PLA as a renewable material and make it more attractive in terms of energy savings from increased reusability of PLA monomers.

Biodegradable PLA is made from renewable resources. This renewability makes PLA a good candidate for high volume disposable plastic products such as water bottles, milk jugs, and other food packaging applications. According to experts, the rise of corn ethanol as transportation fuel has increased the demand for corn grain that would otherwise be available for lactic acid production (*Biodegradable Polymers and Plastics*. Chiellini, Emo; Solaro, Roberto; Eds. (2003)). To make PLA a more successful commercial product, issues related to disposal of PLA (despite its biodegradable nature) need to be further addressed. Increasing the efficiency of PLA depolymerization would be significantly helpful to alleviate issues regarding PLA disposal by allowing the PLA to be recycled into its monomer. This would allow the material to be reused in food contact applications as well as eliminate the need of additional feedstock materials.

Accordingly, there is a need for economical sources of renewable monomers and biodegradable polymers. There is also a need for new and improved methods to recycle PLA, such that less energy is used in such processes than in currently available PLA recycling processes.

SUMMARY

The technology described herein enables the depolymerization of polylactic acid at very high rates, effectively reducing the process/cycle time for the recovery of lactic acid. The technology thereby improves the economics of lactic acid recovery, enabling cost effective recycling of lactic acid. The methods can be used to recover lactic acid from polylactic acid based products such as bottles, food packaging, disposable utensils, and the like.

Accordingly, the invention provides methods for the energy efficient depolymerization of polylactic acid (PLA), such as post consumer polylactic acid, optionally in conjunction with the use of ultrasonics. For example, the invention provides a method to convert polylactic acid to lactic acid or a salt thereof. The method can include contacting solid particles of polylactic acid and an alcoholic solution having certain depolymerization catalysts in the alcoholic solution. The alcoholic solution can include, for example, an alkali metal hydroxide, an alkali metal carbonate, or both. The alcoholic solution can be a $(C_1-C_4)$alcohol, or combinations thereof, such as methanol, ethanol, or a combination thereof. The PLA, the alcoholic solvent, and the depolymerization catalyst is combined to form a first mixture. The first mixture can be maintained at about 30° C. to about 90° C., for a period of time sufficient to depolymerize the polylactic acid of the solid particles, thereby providing lactic acid monomers or salts thereof. The lactic acid monomers or salts thereof can be obtained in an alcoholic solution and can be further isolated and purified according to techniques well known in the art.

In one embodiment, the alcoholic solution comprises methanol.

In another embodiment, the alcoholic solution comprises ethanol.

In one embodiment, the alkali metal hydroxide is lithium hydroxide, sodium hydroxide, potassium hydroxide, or a combination thereof.

In one embodiment, the alkali metal carbonate is lithium carbonate, sodium carbonate, potassium carbonate, or a combination thereof. In further embodiments, combinations of an alkali metal hydroxide and an alkali metal carbonate can be used.

In some embodiments, the polylactic acid depolymerizes at a rate of at least about 1 g PLA/10 minutes/0.5 g alkali metal hydroxide or carbonate.

In some embodiments, the temperature of the first mixture is maintained at about 35° C. to about 85° C., about 40° C. to about 80° C., about 45° C. to about 75° C., about 50° C. to about 75° C., about 50° C. to about 60° C., or about 55° C. to about 75° C.

In one embodiment, the solution comprises an alkali metal hydroxide and methanol or ethanol, the temperature of the first mixture is maintained at about 50° C. to about 60° C., and the polylactic acid is converted to lactic acid at a rate of at least about 1 g PLA/10 minutes/0.5 g alkali metal hydroxide.

In another embodiment, the solution comprises an alkali metal carbonate and methanol or ethanol, the temperature of the first mixture is maintained at about 50° C. to about 60° C., and the polylactic acid is converted to lactic acid at a rate of at least about 1 g PLA/6 minutes/0.5 g alkali metal hydroxide.

The methods allow for obtaining L-lactic acid or a salt thereof in high enantiomeric purity. When the PLA is PLLA, the lactic acid or salt thereof that is obtained can be substantially enantiomerically pure L-lactic acid or a salt thereof.

The alcoholic solution can be substantially anhydrous or completely anhydrous. In some embodiments, it can be advantageous to include small amounts of water, such as about one mole of water for each mole of lactic acid to be obtained. In some embodiments, the alcoholic solution includes less than about 5 wt. % water. In other embodiments, the alcoholic solution includes less than about 2 wt. % water, less than about 1 wt. % water, less than about 0.5 wt. % water, less than about 0.25 wt. % water, less than about 0.1 wt. % water, less than about 0.05 wt. % water, or less than about 0.01 wt. % water.

In some embodiments, the depolymerization rate can be improved by adding a small amount of a co-solvent to the alcoholic solvent. The co-solvent can be about 0.05 to 5% by volume of the alcoholic solvent. Examples of the organic solvent can include, for example, xylenes, toluene, acetonitrile, 1,4-dioxane, tetrahydrofuran, and/or hexane.

The method described herein can further include sonicating the solid particles of polylactic acid to enhance the rate of depolymerization of polylactic acid to lactic acid or salts thereof.

In one embodiment, a combination of $K_2CO_3$, NaOH, and methanol are employed.

In some embodiments, the invention provides a method for using sodium hydroxide (NaOH) and/or potassium carbonate ($K_2CO_3$) in methanol for the depolymerization of poly(lactic acid). The depolymerization is remarkably fast, depolymerizing samples within about 5-7 minutes under moderate conditions (~60° C.). Other poly(lactic acid) depolymerization methods typically require long cycle times (30 minutes to 24 hours), or harsh conditions such as high temperatures and pressures. The reduced cycle time achieved using the methods described herein allows for the recovery of lactic acid from postconsumer PLA products with lower energy requirements, thereby reducing greenhouse gas emissions. The depolymerization of PLA can be accelerated by factors such as temperature and the concentration of the base.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
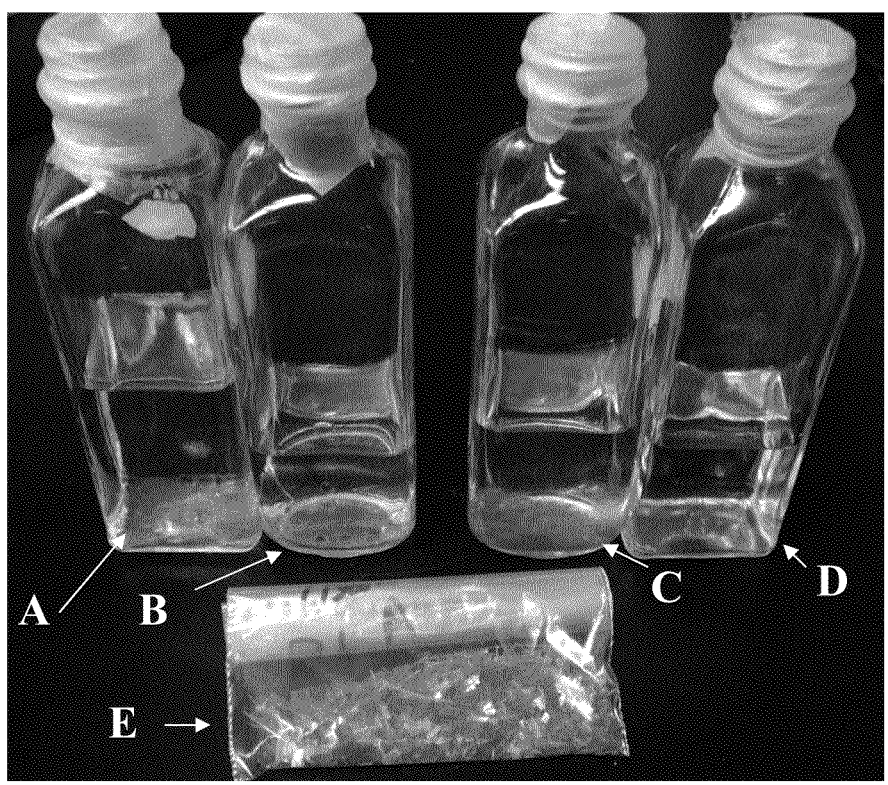
FIG. 1. PLA sample details and treatments: A. Heated bath without depolymerization catalyst; B. Heated bath with depolymerization catalyst; C. Ultrasonic treatment without depolymerization catalyst; D. Ultrasonic treatment with depolymerization catalyst; E. Chopped PLA.

Because of the increased use of polylactic acid (PLA) as a replacement for petroleum plastics, researchers have investigated various methods of lactic acid recovery from PLA.

Most of these depolymerization techniques employ either one or a combination of pressure, heat and catalysts, the combination of which pose a disadvantage to the energy economics of the lactic acid recovery process. Hydrolytic depolymerization has been a popular approach, where pressures of approximately at 10 MPa (~1500 psi) are applied in combination with temperatures ranging between 120-200° C. to depolymerize PLA in small quantities (Yagihash et al., *Ind. Eng. Chem. Res.* 2010, 49, 1247-1251; Watanabe et al., *Macromolecular Theory and Simulations* (2007), 16(6), 619-626). Though the inexpensive treatment media used in this approach is water or a basic solution, scale-up of such high pressure processes make the technique energy intensive. Additionally, hydrolytic depolymerization is a batch process, which renders it inefficient compared to continuous systems.

Other techniques that have been investigated to break down PLA include selective enzymatic depolymerization (Faisal et al., *WIT Transactions on Ecology and the Environment* (2006), 92 (Waste Management and the Environment III), 225-233) and metal salt catalytic depolymerization (Motoyama et al., *Polymer Degradation and Stability* (2007), 92(7), 1350-1358). These methods have issues such as slower conversion rates and higher residue of metal ions, which makes them unattractive as recycling techniques. Thus, the development of an alternate recycling technique that satisfies the needs of the recycling industry, especially economic viability, is critical to the continued acceptance of PLA by manufacturers.

Degradation of PLA occurs as a bulk erosion mechanism and the activation energy for depolymerization changes with temperature. This is indicative of PLA's response to the energy level of its treatment media. Investigation of different treatment media for depolymerization and use of a different approach to initiate depolymerization other than heat and pressure led to significantly improved methods for depolymerizing PLA, as described below.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the molecular level, for example, to bring about a a chemical reaction, or a physical change, e.g., in a solution, in a suspension, or in any mixture such as a reaction mixture.

An "effective amount" refers to an amount effective to bring about a recited effect. For example, an effective amount can be an amount of a reagent or catalyst effective to initiate a reaction and to provide a discernable amount of products, such as lactic acid from polylactic acid. Determination of an effective amount is well within the capacity of persons skilled in the art. The term "effective amount" is intended to include an amount of a compound described herein, or an amount of a combination of compounds described herein, e.g., that is effective to initiate a depolymerization reaction. Thus, an "effective amount" generally means an amount that provides the desired outcome.

The term "substantially anhydrous" refers to a solution that has less than about 5 wt. % water. More preferably, the solution has less than about 4 wt. % water, less than about 3 wt. % water, less than about 2 wt. % water, less than about 1 wt. % water, less than about 0.5 wt. % water, less than about 0.25 wt. % water, less than about 0.1 wt. % water, or the solution is free of water.

The term "lactic acid" refers to a compound of the formula $CH_3CH(OH)CO_2H$. Lactic acid can be one of two optical isomers (L-(+)-lactic acid or (S)-lactic acid, and its mirror image D-(−)-lactic acid or (R)-lactic acid), or the lactic acid can be scalemic or racemic. The term "polylactic acid", "PLA", or "polylactide" refers to thermoplastic aliphatic polyester of the formula $-(CH(CH_3)C(=O)-O)_n-$ where n is such that the molecular weight of the polymer is about 500 to about 1,000,000, and typically about 10,000 to about 1,000,000. Poly-L-lactide (PLLA) is the product resulting from the polymerization of L,L-lactide (also known as L-lactide). The depolymerization methods described herein can be used to depolymerize polylactic acid or a polylactic acid copolymer. Examples of specific homopolymers include poly(L-lactic acid), poly(DL-lactic acid), syndiotactic poly(DL-lactic acid), and atactic poly(DL-lactic acid).

The term "alcoholic solution" refers to a solution where the solvent is an alcohol, such as a $(C_1-C_4)$alcohol. Examples include methanol, ethanol, n-propanol, iso-propanol, n-butanol, iso-butanol, sec-butanol, and tert-butanol.

The term "alkali metal hydroxide" refers to LiOH, NaOH, KOH, or RbOH.

The term "alkali metal carbonate" refers to $Li_2CO_3$, $Na_2CO_3$, $K_2CO_3$, or $Rb_2CO_3$.

The term "depolymerize" refers to a process wherein a polymer is broken down, at least partially, to a plurality of its monomers. For example, depolymerization of PLA results in the production of lactic acid or a salt thereof.

When a method provides salts of lactic acid as a reaction product, the lactate salts can be isolated as lactic acid according to known processes. Examples of such processes include dialysis (see, e.g., Persson et al., *Appl. Biochem. Biotechnol.* 2001 June; 94(3):197-211), acidification and precipitation (see, e.g., U.S. Pat. No. 6,087,532 (Baniel et al.)), ion exchange techniques (see, e.g., U.S. Pat. No. 5,132,456 (King et al.)), adjustment of pH, and extraction, and the like. The lactic acid or lactic acid salt can also be converted into lactide, the cyclic di-ester of lactic acid, according to known methods such as condensation and dehydration techniques (see also U.S. Pat. No. 7,396,667 (Masumura)).

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Depolymerization of PLA

Samples were sourced from a PLA water bottle manufacture (Naturally Iowa, LLC). The walls of the bottle were cut into strips of standard width (~6 mm) using an office paper shredder. These strips were then chopped into 6×2 mm samples utilizing a Scheer Bay BT-25 strand pelletizer (Bay Plastics Machinery, MI). A Branson 2000ea series 20 KHz ultrasonic system (2200 W) was used when samples were treated with ultrasonics. The ultrasonic treatment medias were water, methanol, and ethanol along with various salts and metal bases as follows: potassium carbonate ($K_2CO_3$), sodium hydroxide (NaOH) (Fischer Scientific, Pittsburg, Pa.); aluminum carbonate ($Al_2(CO_3)_3$) (Alfa Aesar, MA); zinc carbonate basic $[ZnCO_3]_2[Zn(OH)_2]_3$; magnesium oxide (MgO); and zirconium(IV)oxide ($ZrO_2$).

Various salts and metal bases were screened and the successful salts were analyzed for further investigation. The total solids and chemical concentrations were varied over a wide range of values to determine an advantageous media composition. Samples with a total volume of 50 mL were exposed to solvent mixtures, sonication, and combinations thereof, in batch modes. A full factorial experimental design was created and conducted with each independent parameter varied as shown in Table 1 below. The table excludes the parameters treatment time and amplitude. A majority of the samples below were treated at 16 μm (peak-peak) amplitude for a maximum time period of 15 minutes or until 100% mass loss. This amplitude was selected as the highest amplitude where a cavitation vapor barrier could be prevented.

TABLE 1

Table of parameters with codes.

| Sample Mass | Code (Pos #1) | Treatment Media | Code (Pos #2) | Catalyst/chemical | Code (Pos #3) |
|---|---|---|---|---|---|
| 1 g | 1 | Methanol | M | $K_2CO_3$ (0.5 g) | K(1) |
| 5 g | 5 | Ethanol | E | $K_2CO_3$ (0.25 g) | K(2) |
| | | | | NaOH (0.5 g) | Na(1) |
| | | | | NaOH (0.25 g) | Na(2) |
| | | | | NaOH (0.125 g) | Na(3) |

All experimental end points were repeated in duplicate sets. The treated sample media (solution) was characterized for lactic acid concentration using high performance liquid chromatography (HPLC). Selected samples were examined using scanning electronic microscopy (SEM). Upon completion of ultrasonic treatment, the suspension sample was separated into solid and liquid components. The recovered dry plastic samples were measured for weight loss and a mass balance analysis was carried out to determine the degree of depolymerization, defined as:

$$\text{Degree of depolymerization} = \frac{(\text{Initial weight} - \text{Post treatment weight}) \times 100}{\text{Initial weight}}$$

Results.

In initial experiments, chopped PLA from water bottles (1 g) was added to methanolic potassium carbonate ($K_2CO_3$), typically having the desired about of base/catalyst in about 40-60 mL of alcoholic solvent, or about 50 mL of alcoholic solvent. One sample was exposed to ultrasonics and the other was agitated in a hot bath (~55° C.). The process was able to de-polymerize PLA in methanol in 12 min using ultrasonics and the $K_2CO_3$ catalyst, compared to the conventional method that required 30 minutes using a hot water bath. See FIG. 1, where little or no PLA remains in samples B and D, which used the alcoholic catalyst system.

Figure 2:
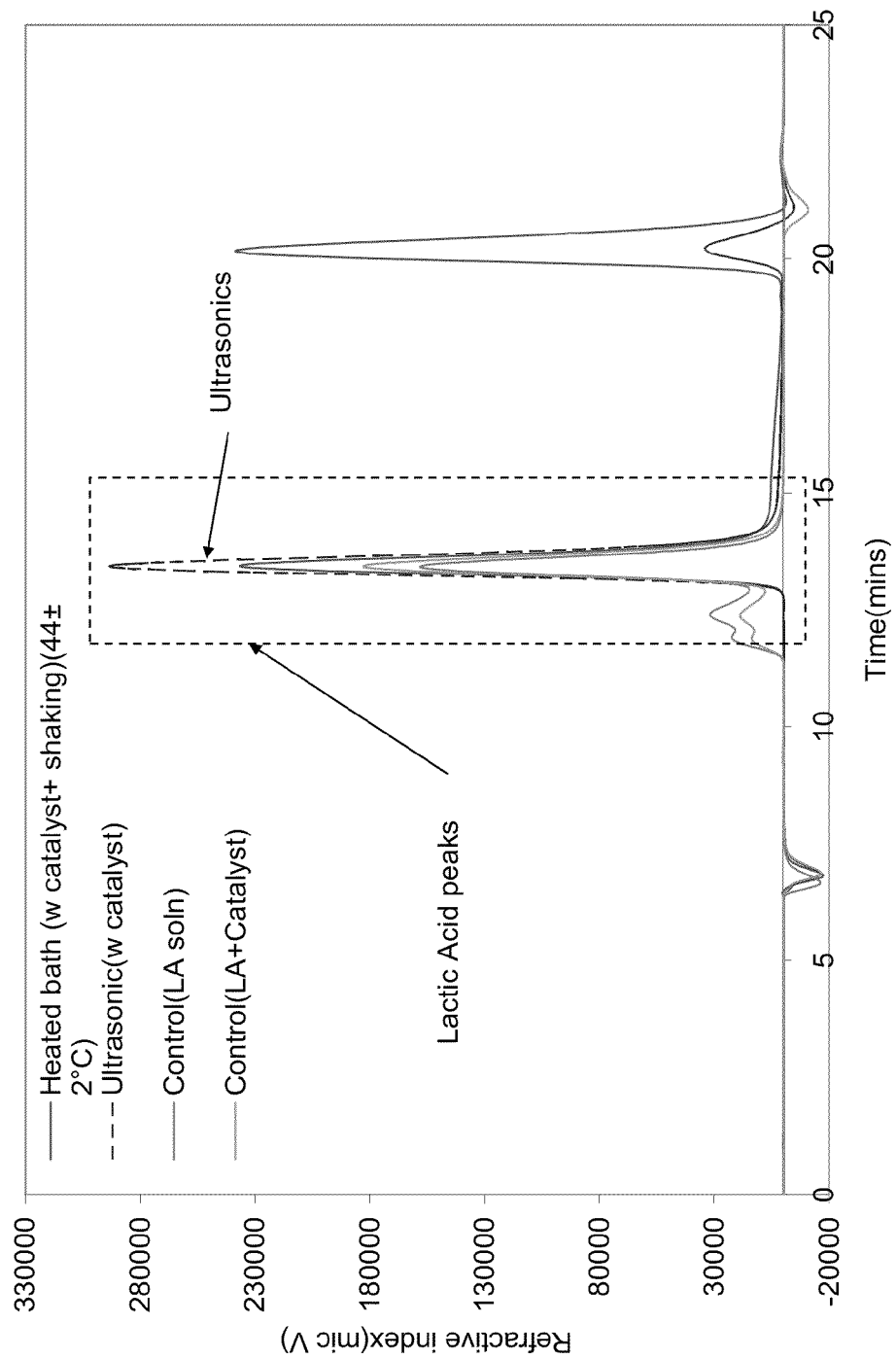
FIG. 2. HPLC analysis of the control solutions and depolymerized PLA solutions using heated bath and ultrasonics, respectively.

The conversion of PLA into lactic acid was confirmed using High Performance Liquid Chromatography (HPLC). In sample D (treated with ultrasonics; FIG. 1), lactic acid peaks were observed at approximately 12-13 minutes after HPLC injection. This peak was consistent with that of the control solution (lactic acid) as seen in FIG. 2. The area under the lactic acid peak of the ultrasonics sample was higher compared to the hot bath hydrolysis. This indicates a higher yield of lactic acid for the ultrasonic treatment with respect to the hot bath process, for the same mass of PLA.

Figure 3:
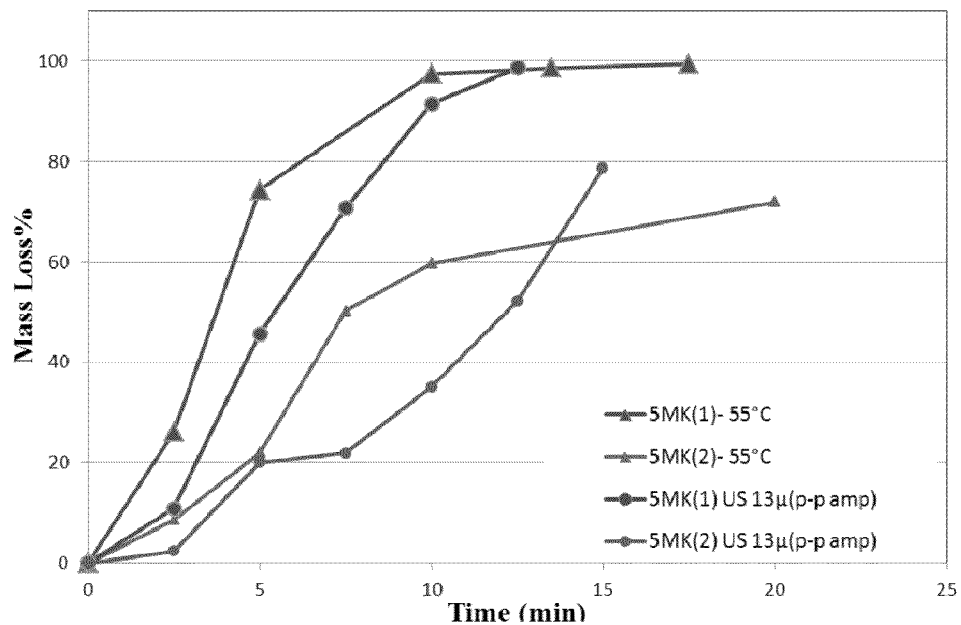
FIG. 3. Mass loss (%) comparison between hot bath and ultrasonic treatment for two concentrations of $K_2CO_3$: K(1)-0.5 g; K(2)-0.25 g.
Figure 4:
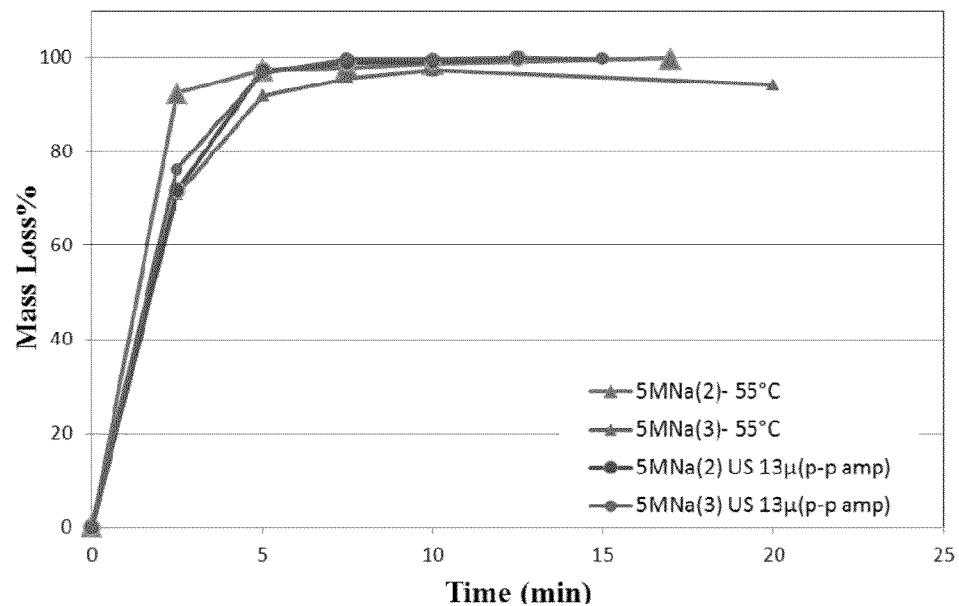
FIG. 4. Mass loss (%) comparison between hot bath and ultrasonic treatment for two concentrations of NaOH: Na(2)-0.25 g; Na(3)-0.125 g.

Based on the results of the screening experiments (Table 1), experiments with 1 g and 5 g samples of PLA were put in a hot bath and treated with ultrasonics in a solution of methanol and $K_2CO_3$ (Table 1 code: MK). As shown by FIG. 3, independent of the treatment and conditions, the mass loss of PLA (conversion to lactic acid) asymptotically approaches 100% as a function of time. In addition, for both the 1 g and 5 g samples, the rate of depolymerization is not significantly affected by the ultrasonic treatment ("US"). For the 1 g samples, PLA can be fully depolymerized in approximately 10 minutes. A temperature of 55° C. was selected because this was similar to the temperature achieved during the ultrasonic treatment. A similar trend is found with methanolic NaOH (FIG. 4), however the conversion time is only approximately 6 minutes.

Figure 5:
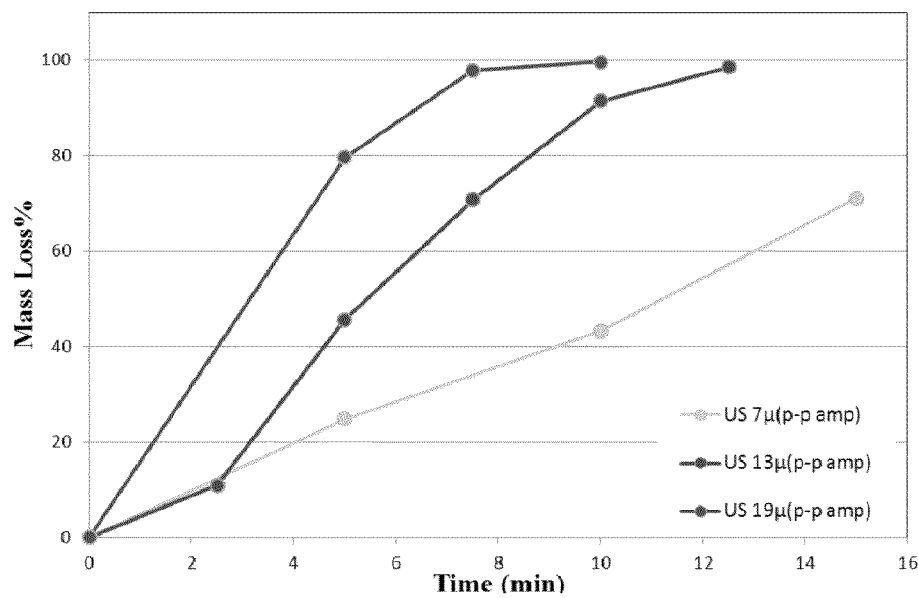
FIG. 5. Relative mass loss (%) as a function of treatment time for MK experiments using various ultrasonic amplitudes (7, 13 and 19μ); 0.5 g $K_2CO_3$ and methanol.

FIG. 5 shows PLA depolymerization, as determined by mass loss, as a function of time for three amplitudes. The depolymerization is generally proportional to time and asymptotically approaches 100%. The rate of depolymerization is also generally proportional to the amplitude.

To gain insight into why ultrasonic treatment did not significantly affect the reaction rates as seen with many other reactions, optic and scanning electron microscopy studies were completed. It was optically determined that the particle size was not significantly altered by ultrasonic treatment. Typically, particle size is reduced when particulate substrates (such as chips) are treated in a liquid ultrasonic bath. The treatment typically increases the surface area to volume ratio and increases the number of reaction sites, increasing reaction rates. This was not observed with the treated PLA chips and it believed to be a result of the toughness of the plastic and its ability to absorb shock waves produced by the ultrasonic cavitation.

Figure 6:
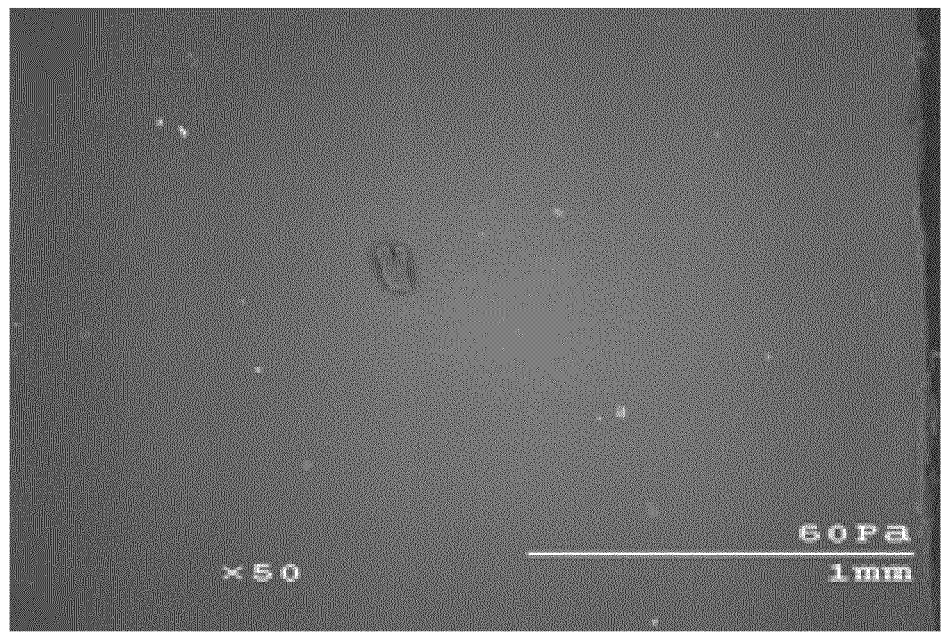
FIG. 6. Scanning electron microscopy (SEM) image of an untreated PLA sample.
Figure 7:
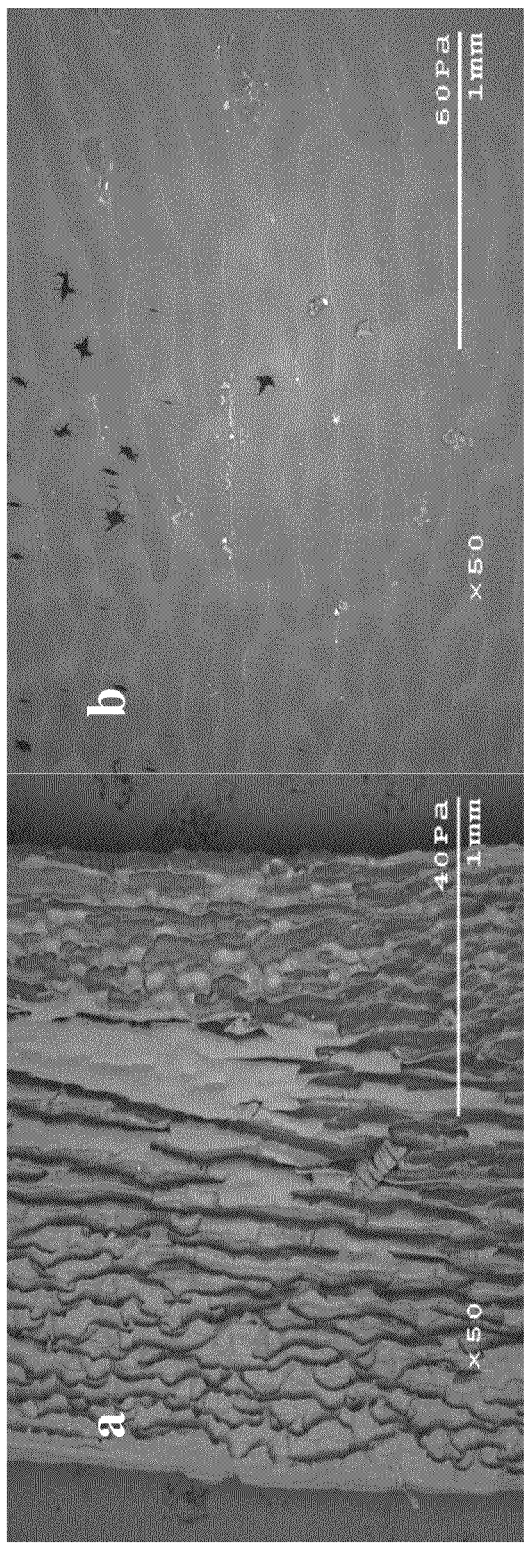
FIG. 7. Treated PLA sample at 5 minutes with NaOH-0.25 g and methanol media (0.5 g): (a) Ultrasonics-13μ; (b) Hot bath.

FIG. 6 shows an SEM image of virgin PLA as received. The surface is relatively smooth. However after 5 minutes of depolymerization treatment with NaOH-0.25 g and methanol media the surfaces become rough, as shown in FIG. 7. After ultrasonic treatment there is a very rough texture on the particle surface and the alignment of this texture corresponds to the stretch direction of the PLA bottle from which the chip originated. This texture was more pronounced on the inner diameter of the bottle where the degree of crystalline is higher due to slower cooling. The texture is also less pronounced in hot bath treated samples. The ultrasonics appears to have enhanced mixing of liquids and to have caused some cavitation erosion on the particle surface. These effects resulted in the rough surface but the increase in the surface area was not sufficient to significantly accelerate depolymerization.

A similar effect was observed with $K_2CO_3$-0.5 g and methanol. However, both the hot bath and the ultrasonic surfaces formed similar roughness. While the ultrasonically treated samples appear to be slightly rougher in appearance, they are overall similar. The mixing effects of ultrasonics affected the chemical pathways but were not sufficient to significantly accelerate the chemical depolymerization rates.

Conclusions.

While ultrasonics typically increases reaction rates by many fold, this effect was not observed with the depolymerization of PLA chips. Chip size was not reduced during sonication. In many reactions involving liquid/solid phases, particle size (chip size) reduction is often observed during sonication, which increases the surface area to volume ratio. A reduced particle size can therefore increase the number of possible reaction sites and increase reaction rates. Such effects were not observed in this study of PLA and alkaline alcoholic solutions. The major controlling factors for depolymerization of PLA were the type of catalyst used, temperature, and crystallinity of the PLA.

Example 2

Recycling of Lactic Acid from Postconsumer PLA Products

A first phase of trials for recycling lactic acid from postconsumer PLA products involved an array of screening experiments. Based on the outcome of these trials, further confirming tests were designed and conducted. These outcomes were compared to identify the design space for process optimization of the operating parameters. The various experimental materials, methods, and testing equipment used in the research are detailed below.

1.1 Materials.

1.1.1 Raw Material and Preparation: Post Consumer Poly Lactic Acid Polymer.

The raw PLA material for this work was sourced from Totally Green Inc., IA, previously known as "Naturally Iowa". The source was postconsumer PLA water bottles from the company's packaged water product brand "Green Bottle Spring Water". It should be noted that the bottles were made with the Ingeo™ PLA resin, which is manufactured by NatureWorks LLC (Blair, Nebr.). The PLA bottles were washed and rinsed with warm water (45° C.) to remove dirt and beverage residues. Further, the bottles were steeped in room temperature water for approximately 3 hours to facilitate the removal of the brand label on the bottle. Following label removal, the bottles were rubbed with denatured ethanol to complete the removal of residual adhesive from the product label.

The bottles were air dried for 2 days to remove any residual water from the washing process. The bottles were then chopped into PLA chips with standard dimensions. The thickness of the chips was limited by the capacity of the chopping equipment used to cut the samples. To avoid variation in the thickness of the PLA chips, the uniformly thick tubular section of the bottle was used, discarding the bottom and the neck sections which were found to be uneven in thickness. Further, the tubular portion was cut open into sheets and fed to a strip-cut paper shredder that produced strips with a standard width of ~6 mm. These strips were chopped into chips of 6 mm×2 mm in dimension using a BT-25 strand pelletizer from Scheer Bay Plastics Machinery.

1.1.2 Chemical Compounds and Treatment Media.

The ultrasonic treatment of PLA chips was completed with various salts and treatment media. The various salts and compounds used were potassium carbonate ($K_2CO_3$), calcium carbonate ($CaCO_3$), and sodium hydroxide (NaOH), all obtained from Fischer Scientific in Pittsburg, Pa.; aluminum carbonate ($AL_2(CO_3)_3$) from Alfa Aesar, MA; zinc carbonate basic $[ZnCO_3]_2 \cdot [Zn(OH)_2]_3$, magnesium oxide (MgO), and zirconium(IV)oxide ($ZrO_2$) catalyst from Sigma Aldrich, MO; and copper(II) carbonate, basic ($CuCO_3 \cdot Cu(OH)_2$) from Strem Chemical, MA. Most of these compounds are carbonates and oxides of alkali, alkaline earth, and transition metals, selected because they are weak electronegative metals. When ionized, they yield cations that should produce a reactive species that will react with the PLA intramolecular bonding. In addition, in proof of concept trials, carbonate salt of potassium proved to be highly effective in methanol. The three media used for this research were water, methanol, and ethanol. Though none of these media are solvents of PLA, they were selected because LA is soluble or miscible in them. It was envisioned that if depolymerization of PLA into lactic acid occurred, the collection and purification of the lactic acid would be easier utilizing these media. The separation of lactic acid from these media can be achieved by low temperature distillation due to their relatively low boiling point temperatures (except for water). L(+)-Lactic acid (90%) from Acros Organics, NJ, was utilized for the construction of the standard curve to measure the Lactic acid concentration in samples.

1.2 Methods.

1.2.1 Methods: Ultrasonic Treatment.

Ultrasonic treatment of PLA samples were conducted with a Branson 2000ea series 20 KHz ultrasonic system (2200 W), with an ultrasonics stack. The system was equipped with an ultrasonic stack that consisted of a PZT transducer (20 KHz, maximum amplitude of 20 $\mu m_{p-p}$), a booster with a gain of 1:0.6 signal multiplying factor (a reducing booster), and a horn (1:2.17 multiplying factor) with a 39 mm diameter flat face. The stack assembly produced an amplitude of 26 $m\mu_{p-p}$ at 100% power. All the samples were treated in a 150 mL quartz beaker. Samples consisted of the PLA sample mass (1 g to 5 g), catalyst compound (0.125 g to 0.5 g), and 50 mL of the treatment medium respectively. The temperatures of the sonicated samples were recorded during treatments. Experiments were conducted in three phases, as discussed in the following sections.

1.2.2 Thermo-Gravimetric Analysis.

To gain insight of material composition and thermal properties, PLA analysis was carried out on a thermo gravimetric analyzer (TGA) from TA Instruments, New Castle, Del. A heating rate of 10° C./min was used for TGA analysis.

1.2.2.1 Ultrasonic Treatment: Phase-I (Screening Experiments).

Ultrasonic treatment of PLA samples were conducted with all possible permutations of the parameters listed in Table 2-1 (chemical compounds and treatment media). The table also displays the code structure used for the nomenclature of individual experiments. For example, experiment "1MK(1)15X" indicates that 1 g of PLA chips in treatment media methanol "M" with catalyst potassium carbonate (0.5 g) "K(1)" was treated for a time of 15 min at an amplitude of 13 $\mu m_{p-p}$, or a power level of 50%.

TABLE 2-1

Matrix of variables used during Phase-I.

| | Sample Mass | | Treatment Media | | Catalyst | | Time | | Amplitude | |
|---|---|---|---|---|---|---|---|---|---|---|
| S. No | Mass | Code (Pos #1) | Media | Code (Pos #2) | Type | Code (Pos#3) | Min | Code (Pos #4) | $\mu_{p-p}$ | code (Pos #5) |
| 1 | 1 g | 1 | Methanol | M | $K_2CO_3$(0.5 g) | K(1) | 15 min | 15 | $7\mu_{p-p}$ | W |
| 2 | | | Water | W | $K_2CO_3$(0.25 g) | K(2) | 20 min | 20 | $13\mu_{p-p}$ | X |
| 3 | | | Ethanol | E | $AL_2CO_3$ | Al | 10 min | 10 | $19\mu_{p-p}$ | Y |
| 4 | | | | | $Zn_2CO3$ | Zn | 25 min | 25 | | |
| 5 | | | | | NaOH(0.5 g) | Na(1) | 30 min | 30 | | |
| 6 | | | | | NaOH(0.25 g) | Na(2) | | | | |
| 7 | | | | | NaOH(0.125 g) | Na(3) | | | | |
| 8 | | | | | ZrO | Zr | | | | |
| 9 | | | | | MgO | Mg | | | | |
| 10 | | | | | $CaCO_3$ | Ca | | | | |
| 11 | | | | | $CuCO_3$ | CU | | | | |

It should be noted that the treatment parameters, amplitude, and time were fixed at 13 $\mu m_{p-p}$ and 15 min respectively. This was because during screening experiments no acoustic streaming or mixing was observed at an amplitude below 7 $\mu m_{p-p}$. Conversely, at an amplitude above 19 $\mu m_{p-p}$, a vapor barrier was observed to develop between the horn tip and the PLA chips with methanol and ethanol as the media. These effects prevented experiments from being conducted at amplitudes below and above 7 $\mu m_{p-p}$ and 13 $\mu m_{p-p}$, respectively. The treatment time was limited to 15 min for the screening phase, as lower depolymerization times were observed during the proof of concept trials.

The array of experiments was completed to identify the combinations that effected PLA degradation/depolymerization. The degradation/depolymerization of PLA was recognized and quantified by relative weight loss (as a percentage) of the treated sample, which was calculated as defined by Eq. 10.

$$\text{Degree of depolymerization} = \frac{(\text{Initial weight} - \text{Post ultrasonic treatment weight}) \times 100}{\text{Initial weight}} \qquad \text{Eq. 10}$$

Figure 9:
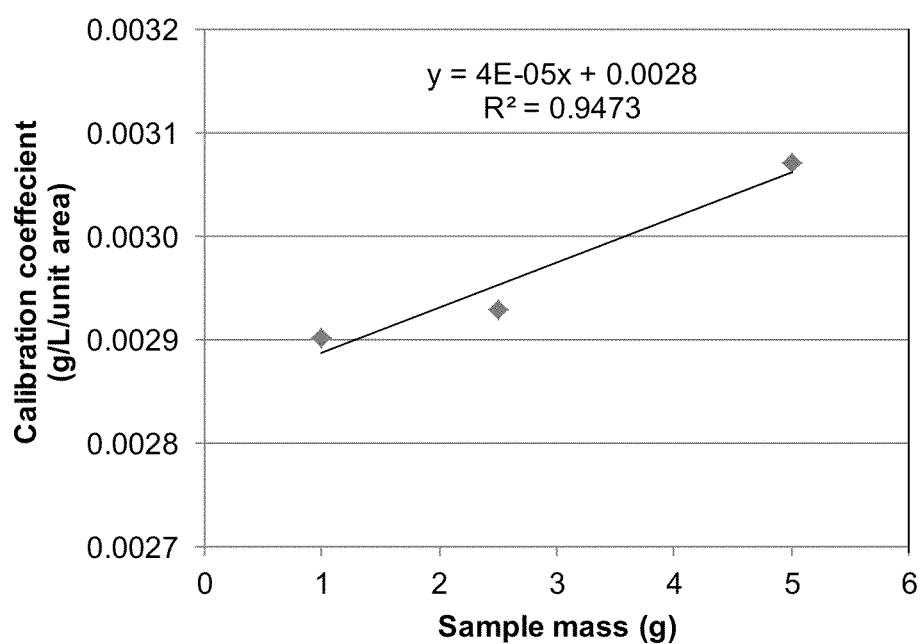
FIG. 9. Calibration coefficient as a function of samples mass.

Further confirmation and quantification of lactic acid was completed with high performance liquid chromatography (HPLC) as a characterization tool. The lactic acid concentration in a treated sample was determined using a calibration coefficient based on the area of LA peaks of known concentration from HPLC as seen in FIG. 9. The linear fit is reasonably good with an $r^2$ value of 0.95. The relation between area of LA peak from HPLC and concentration was established by constructing a standard curve with L(+)-Lactic acid (90%) at concentrations of 1, 2.5 and 5 g per 50 mL.

1.2.2.2 Ultrasonic Treatment: Phase-II (Effect of Sample Mass).

At the completion of Phase-I, the respective combinations of salts and media that resulted in a PLA degradation (mass loss) value greater than 5% were selected for further investigation. Phase-II experiments were conducted by varying PLA chips mass/concentration (1 g to 5 g), along with the respective salt and media combinations identified from Phase-I. The objective of Phase-II experiments was to investigate the effect of initial PLA mass fraction on depolymerization. Based on the results of the PLA mass fraction study, a detailed study of depolymerization as a function of treatment time was conducted.

TABLE 2-2

Matrix of variables used during Phase-III.

| Sample Mass | Code (Pos #1) | Treatment Media | Code (Pos #2) | Catalyst/chemical | Code (Pos#3) |
|---|---|---|---|---|---|
| 5 g | 1 | Methanol | M | $K_2CO_3$(0.5 g) | K(1) |
| | | Ethanol | E | $K_2CO_3$(0.25 g) | K(2) |
| | | | | NaOH(0.5 g) | Na(1) |
| | | | | NaOH(0.25 g) | Na(2) |
| | | | | NaOH(0.125 g) | Na(3) |

2.2.2.3 Ultrasonic Treatment and Hot Bath: Phase-III (Degradation as a Function of Treatment Time).

The best PLA mass fraction (of the ranges studied) from Phase II experiments was identified to be 5 g/(50 mL of media). All further replicates and experiments were conducted with 5 g PLA as the sample mass. The progressive depolymerization of PLA was traced by completing experiments with evenly spaced treatment times (0, 2.5, 5, 7.5 . . . 15 min). The parameters used for Phase-III experiments were derived from the results of Phase-II and are detailed in Table 2-2. A full factorial experimentation of these parameters was conducted to complete the data collection for the ultrasonic treatment experiments.

Figure 10:
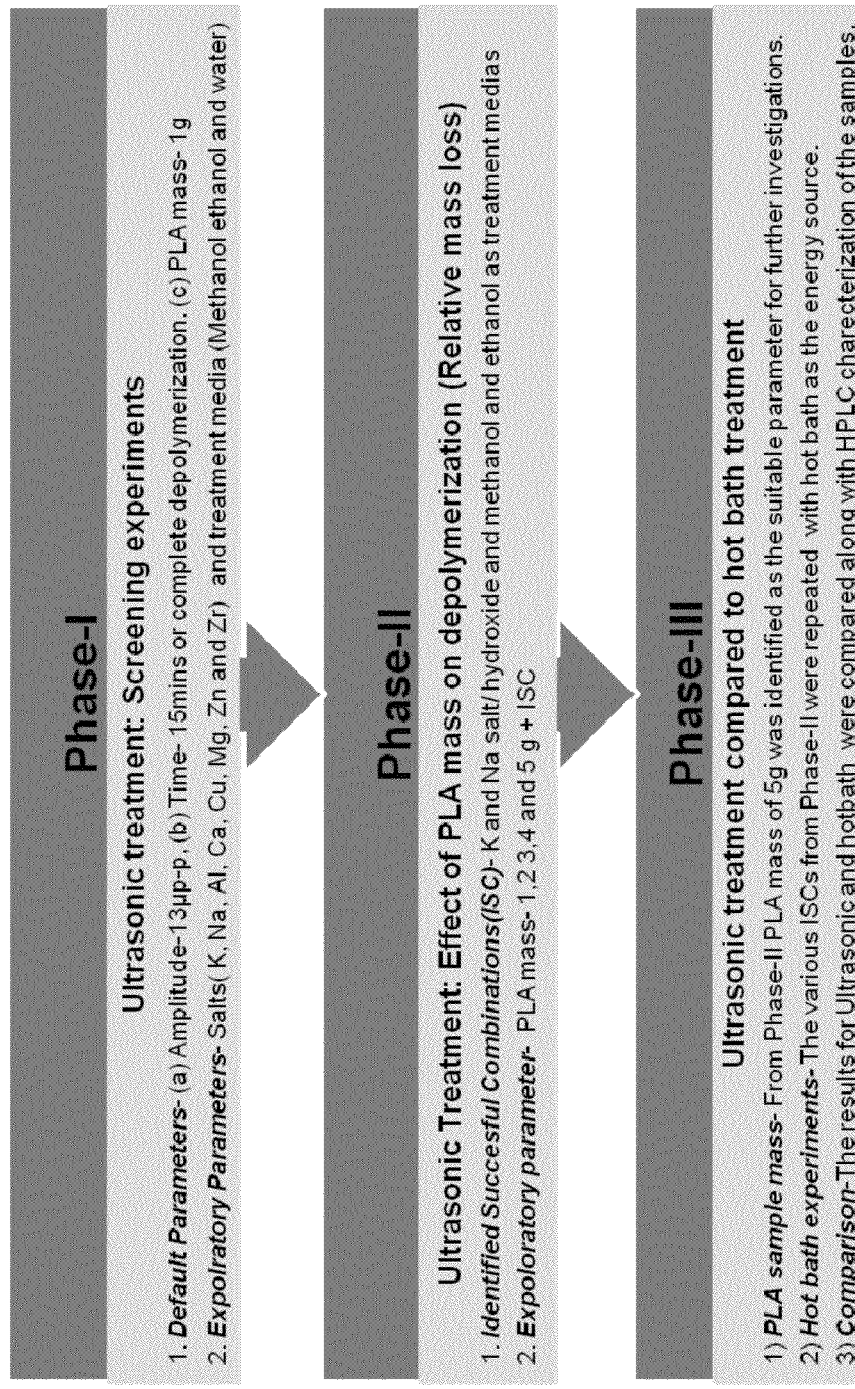
FIG. 10. Flow diagram of overall experimental design, according to an embodiment.

Further experiments were completed for the parameters in Table 2-2 using a hot bath in place of ultrasonics as the energy source (a control group). The hot bath experiments were conducted at the same temperature values observed during the ultrasonics treatment. These temperatures were 55° C. and 65° C. for methanol and ethanol respectively. Because there was fluctuation in the temperatures measured during ultrasonic treatment (±10° C.), the effect of temperature on depolymerization/degradation of PLA was further investigated with the hot bath at temperatures of ±10° C. (above and below) the observed ultrasonic treatment temperatures. A schematic of all three phases and the process flow of the experimentation is illustrated in FIG. 10.

1.2.2.4 Lactic Acid Detection and Quantification—High Performance Liquid Chromatography.

The liquid samples from both ultrasonic treatment and hot bath experiments were filtered with Whatman paper (spec #1). The filtrate was further centrifuged at 6,000 rpm to settle any suspended PLA or salt particles. These centrifuged samples were diluted by a factor of 10 prior to HPLC analysis. The samples were diluted to suppress the peaks that correspond to treatment media concentration (methanol/ethanol) at HPLC. The analysis was completed with a Varian HPLC and Varian-356-LC Ri detector. The column used was Aminex HPX-87H Column #125-0140 for organic acids from Biorad. Standard chemical grade LA samples were used for calibration.

1.2.2.5 Modeling Fluid Flow Caused by Ultrasonics.

The modeling of fluid flow (acoustic streaming) caused by ultrasonics was completed using both real-time tracking with particle image velocimetry (PIV) and virtual modeling with finite element analysis (FEA), Ansys®. Both approaches used water at room temperature and atmospheric pressure as the medium.

1.2.2.5.1 Tracking Fluid Flow Caused by Ultrasonics: Particle Image Velocimetry (PIV).

Figure 11:
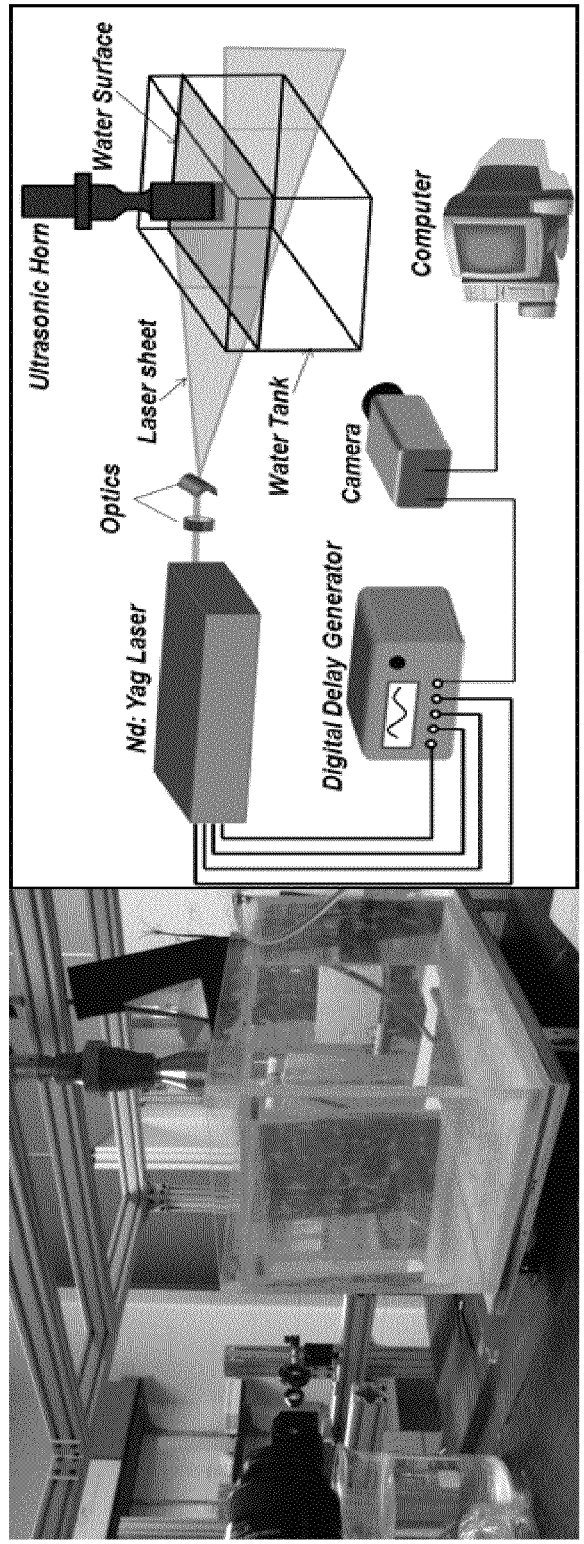
FIG. 11. Photograph and schematics of experimental setup of ultrasonics with PIV investigation.

The fluid flow caused by ultrasonics in water was tracked by adding titanium dioxide ($TiO_2$) beads (Ø 1 μm) to the media. A laser was pulsed through the water to track the movement of the. The water was contained in a transparent acrylic tank of dimensions (L×W×D) of 584 mm×280 mm×278 mm. The setup for the experiment is illustrated in FIG. 11. The ultrasonic horn had a 39 mm dia. flat-faced standard horn, and the ultrasonic system was a 20 kHz system manufacture by Branson Ultrasonic (Danbury, Conn.).

In further detail, the system functions by passing a double-pulsed Nd:YAG laser (NewWave Gemini 200) through a medium, adjusted on the second harmonic and emitting two pulses of 200 mJ at the wavelength of 532 nm with a repetition rate of about 1 Hz. The laser beam was shaped to a sheet by a set of optics with spherical and cylindrical lenses. The thickness of the laser sheet in the measurement region was approximately 1.0 mm. A high-resolution 14-bit CCD camera (PCO2000, 2048×2048 pixels, Cooke Corp) was used for PIV image acquisition, with the axis of the camera perpendicular to the laser sheet. The CCD camera and the double-pulsed Nd:YAG lasers were connected to a workstation (host computer) through a digital delay generator (Berkeley Nucleonics, Model 565), which controlled the timing of the laser illumination and the image acquisition.

Instantaneous PIV velocity vectors were obtained by a frame-to-frame cross-correlation technique involving successive frames of patterns of particle images in an interrogation window of 32×32 pixels. An effective overlap of 50% of the interrogation windows was employed in PIV image processing. Because the FPS (frame per second) of the camera was relative low (approximately 1 Hz), the resulting sampling rate of PIV was approximately 0.97 Hz. The time interval between two sequential images was 600 μs. The image of the illuminated particles captured with a CCD collecting the sequential images were processed with a proprietary software package. Based on spatial locations of the particles from frame to frame, the software calculates the velocities of the particles. These velocities are then plotted as contour plots, which were later used for validating with results from fluid flow simulation results from finite element analysis.

1.2.2.5.2 Modeling Fluid Flow Caused Ultrasonics: Finite Element Analysis (FEA) package.

Figure 12:
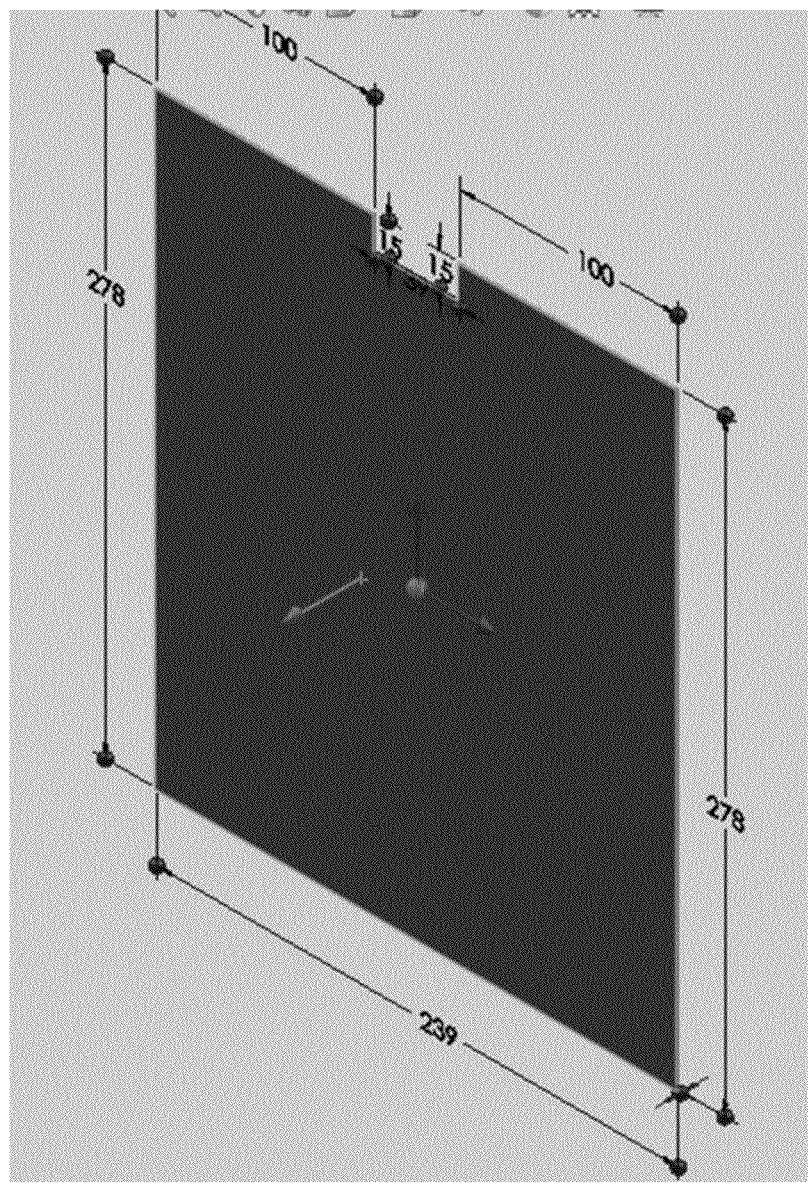
FIG. 12. One element thick beaker model utilized for FEA (units: mm).
Figure 13:
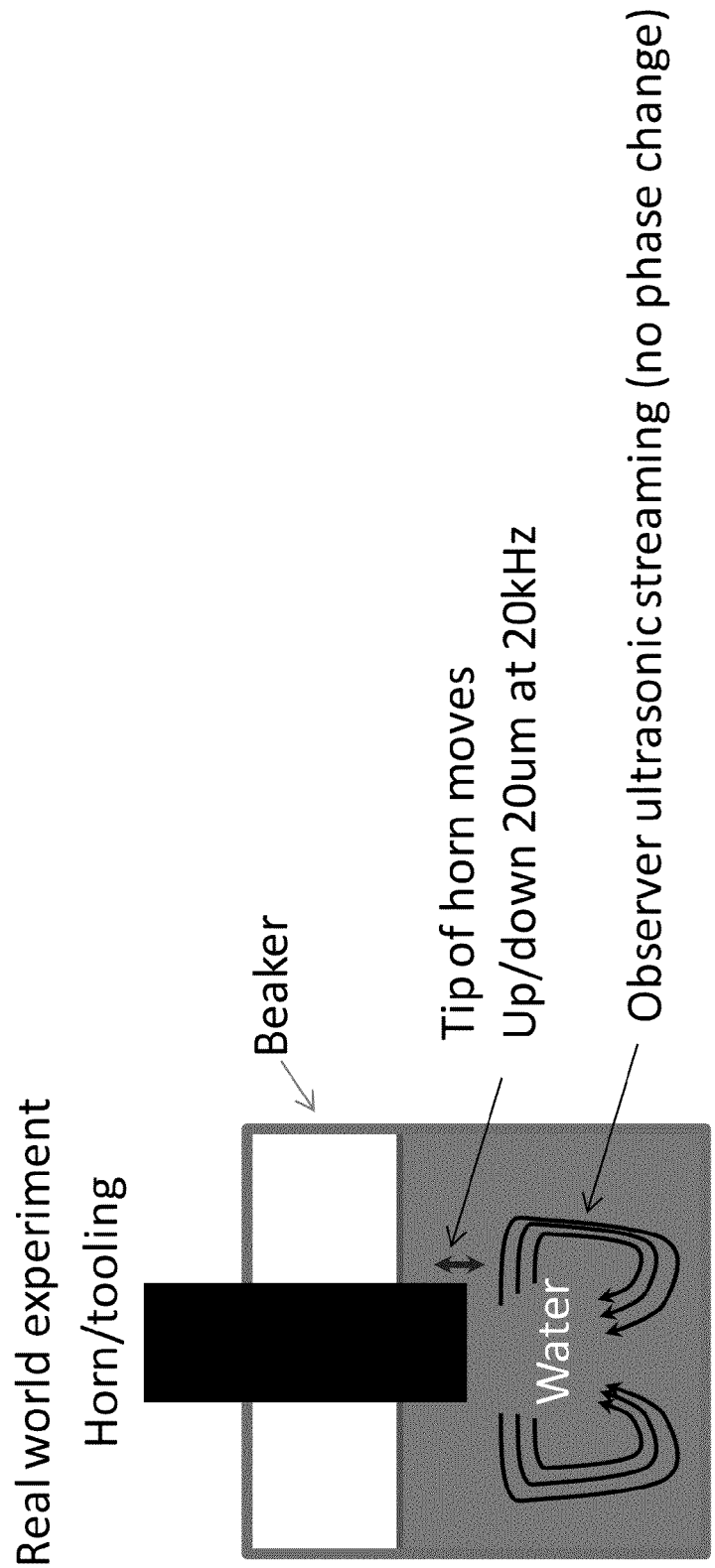
FIG. 13. Illustration of experimental setup that was modeled to predict acoustic streaming.

Finite element analysis (FEA) was used to predict acoustic streaming velocities, and the model was verified with natural buoyancy particle tracking. The FEA was completed with ANSYS Workbench of (Canonsburg, Pa.) version 12.1. The model was constructed in a quasi-2-dimensinal (2D) domain. A 2-D element type was used with an extruded thickness of 1 mm, and the constraints (properties) of the element were defined so that there was no gradient through the thickness of the element. A full-scale model was constructed (2D) through center of the experimental setup, as is detailed in FIG. 12. The model was used to predict the velocity fields in a water bath, as shown in FIG. 13.

The assumptions of the model were: 1) No slip conditions at all interfaces; 2) Newtonian fluid flow with properties defined as water (ANSYS default values); 3) Density of water for fluid; 4) No thermal effects; 5) No phase changes; 6) Atmospheric pressure at the water/air interface; and 7) Horn interface displaces as a function of time to match experimental conditions.

Figure 14:
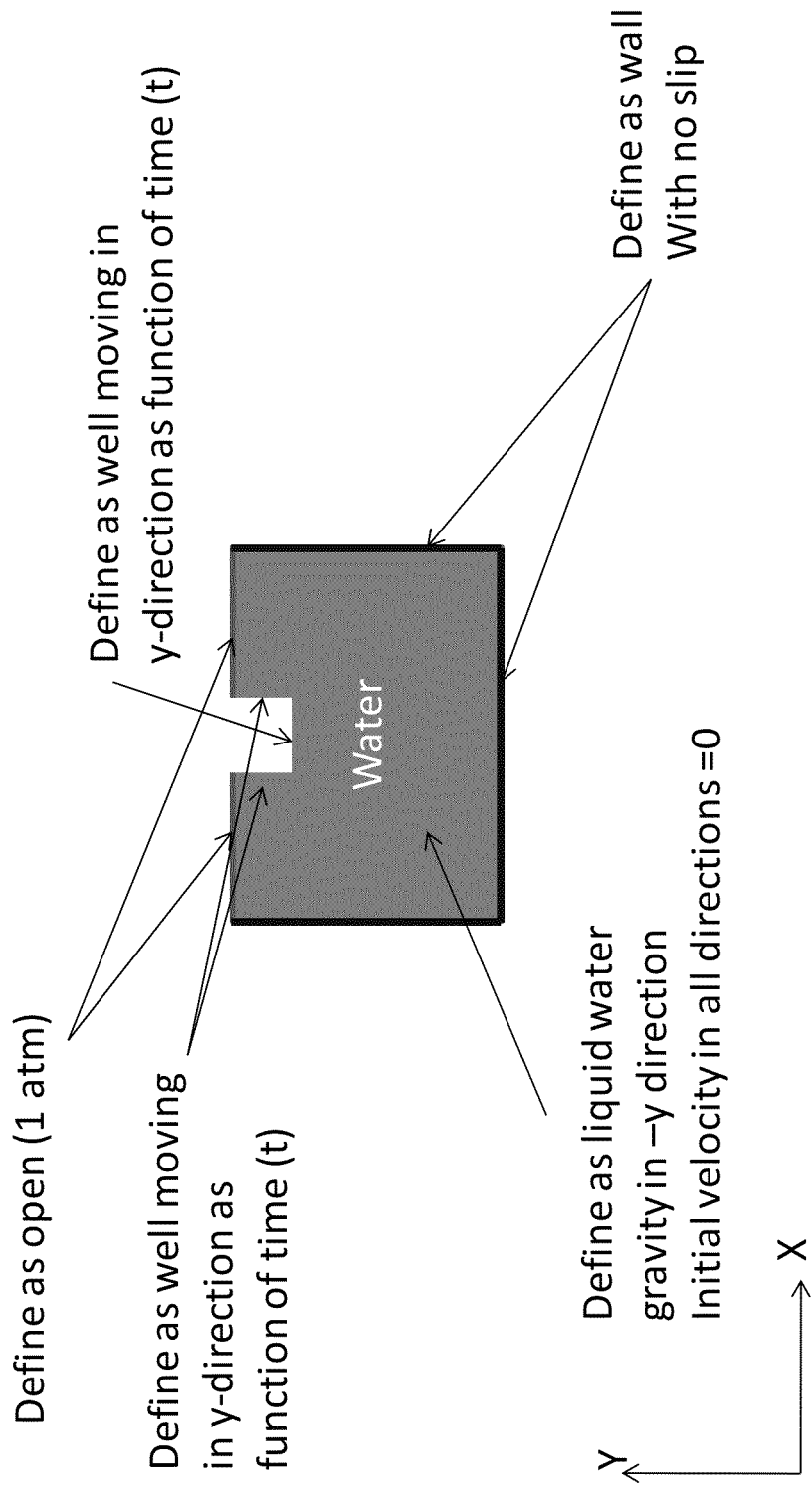
FIG. 14. Details of FEA model assumption and application of the assumptions.

The model was calculated from a static condition and ran for 200 mS. FIG. 14 details some of the assumptions, as well as where some of the boundary conditions were applied. Contour plots of the predicted velocity fields were generated with three varying ultrasonic amplitudes 7, 13, and 19 μm.

1.2.2.6 Scanning Electron Microscopy.

Characterization was done using a Hitachi S-2460N variable pressure scanning electron microscope (VP-SEM). Variable pressure mode allows for examination of insulating samples with minimal sample preparation. A residual atmosphere of 40 Pa (0.3 Torr) of helium is adequate to eliminate charging from most samples while allowing reasonably high magnifications (up to 3000×). The actual pressure is indicated in the lower right of the images (the scope may also be operated in high vacuum (high resolution) mode like a conventional SEM).

Samples were examined at 20 kV using the backscattered electron (BSE) signal (less sensitive to topography than the secondary electron signal, but it is the only signal available with operating this microscope in V-P mode). Images were collected at 50× and 300× magnifications to show the gross and finer details of the texture. Note that some of the low magnification images show little structure, but the structure consists of broad, concave depressions on the surface.

2. Results and Discussion.

As discussed above, the three phases of experiments, including the screening phase, were completed as detailed in FIG. 10. As previously mentioned, these experiments were conducted to refine the design space of the independent parameters. It is important to note that the results from the ultrasonic experiments were compared with hot bath experiments (Phase III) that served as the control group. The results are detailed in the following sections in chronological order of the research phases conducted.

2.1 Results-Phase I.

Phase I experiments were conducted with a default ultrasonic treatment parameter set of amplitude 13 $\mu m_{p-p}$ and treatment time of 15 min. These parameters were based on the results of preliminary data. For all experiments the amplitude was fixed at a value of 13 $\mu m_{p-p}$. In amplitude screening experiments, for amplitudes below 13 $\mu m_{p-p}$, (7 $\mu m_{p-p}$) no streaming was observed. In order to record the effects of amplitude, experiments with methanol and potassium carbonate with various ultrasonic amplitudes (7, 13 and 19 $\mu m_{p-p}$) were completed, the results of which are depicted in FIG. 5. LA yield is generally proportional to treatment time and amplitude. However, because of issues related to vapor barriers limitation, amplitudes above 19 $\mu m_{p-p}$ were not possible to investigate. Thus, the center value of amplitude (13 $\mu m_{p-p}$) was selected as experimental value for the balance of screening experiments.

The various exploratory parameters were investigated in different combinations, as detailed in Table 2-3. The notations MK and MNa indicate that the experiments both had methanol "M" as the treatment medium, with K and Na denoting potassium carbonate and sodium hydroxide as the salt/catalyst respectively. The numbers indicated in parenthesis after the salt notation denotes the mass of the salt. The notations (1), (2), and (3) indicate that the mass of salt/catalyst was 0.5, 0.25, and 0.125 g, respectively. As an example, MK(1) denotes the experiment had methanol "M", potassium carbonate with a mass of 0.5 g and "K(1)" as the treatment medium and catalysts respectively. It was observed that potassium carbonate with masses of 0.25 g and 0.5 g was effective with methanol (MK) in depolymerizing 1 g of PLA but not with ethanol (EK) as the treatment medium. Sodium hydroxide was effective with either methanol (MNa) or ethanol (ENa) as the treatment medium. Both potassium carbonate and sodium hydroxide were ineffective with water as the medium.

TABLE 2-3

Phase1 results: Various combinations of catalysts and treatment media (with codes) marked +ve (effected PLA mass loss), −ve (no mass loss observed), and n.a. (not applicable or not conducted). Default ultrasonic treatment parameters amplitude: 13 $\mu m_{p-p}$, treatment time-15 min or complete depolymerization, PLA mass- 1 g.

| Catalyst | Code | Media Methanol M | Water W | Ethanol E |
|---|---|---|---|---|
| $K_2CO_3$(0.5 g) | K(1) | +ve | −ve | −ve |
| $K_2CO_3$(0.25 g) | K(2) | +ve | −ve | −ve |
| $AL_2CO_3$ | Al | −ve | −ve | −ve |
| $Zn_2CO3$ | Zn | −ve | −ve | −ve |
| NaOH(0.5 g) | Na(1) | n.a. | −ve | +ve |
| NaOH(0.25 g) | Na(2) | +ve | −ve | +ve |
| NaOH(0.125 g) | Na(3) | +ve | −ve | n.a. |
| ZrO | Zr | −ve | −ve | −ve |
| MgO | Mg | −ve | −ve | −ve |
| $CaCO_3$ | Ca | −ve | −ve | −ve |
| $CuCO_3$ | CU | −ve | −ve | −ve |

It should be noted that the experiments with 0.5 g of sodium hydroxide with a methanol medium was not conducted because complete depolymerization of PLA was observed within 5 min of treatment time at a lower mass of 0.25 g of sodium hydroxide. That is, because the lower mass of catalysts resulted in effective depolymerization, it was determined that higher masses (concentrations) would not be justified in terms of optimization. In addition, experiment ENa with a mass of 0.125 g of sodium hydroxide was omitted because the depolymerization was similar to that with the potassium carbonate in that lower masses of the catalysts were effective in depolymerization of PLA. Thus, overall, methanol and ethanol as treatment media with sodium hydroxide and potassium carbonate as catalysts were selected as the design space for further optimization.

2.2 Results-Phase II.

Figure 15:
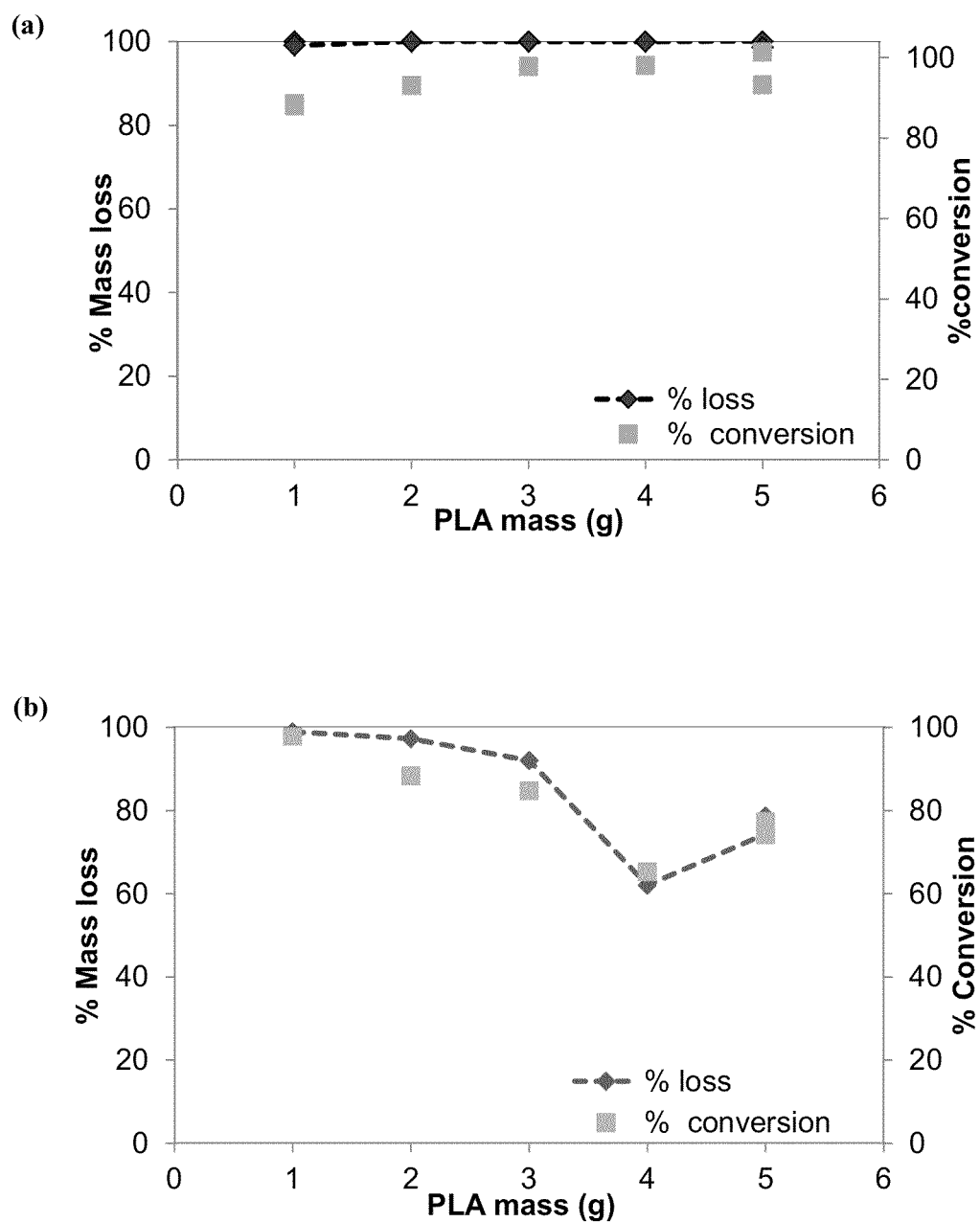
FIG. 15. Relative mass loss (%) as a function of PLA mass for MK experiments (a) for 0.5 g potassium carbonate and (b) 0.25 g potassium carbonate.

Similar to Phase-I experiments, the default ultrasonic treatment parameter set of amplitude 13 $\mu m_{p-p}$ and maximum treatment time of 15 min were used in Phase-II experiments. Again, based on the phase I experiments, the combinations of potassium carbonate with methanol media (MK) and sodium hydroxide with both methanol and ethanol media (MNa and ENa) were used. Phase-II experiments investigated the effect of PLA mass (concentration) from 1 g to 5 g, with 1 g increments. The MK experiments were observed to result in 100% mass loss of PLA at all masses of PLA (1 g to 5 g). In more detail, as seen in FIGS. 15(a) and (b), the results with methanol and at two mass levels 0.5 g (a) and 0.25 g (b) of potassium carbonate indicate that higher levels of catalyst (0.5 g) resulted in 100% mass loss over the entire range of PLA masses studied. In contrast, the lower catalysts mass 0.25 g only resulted in complete levels of mass loss with 2 g or less of PLA. A trend line was added to the mass loss data points for visualization purposes only.

The relative mass loss (relative degree of depolymerization) is consistent with lactic acid concentration measures from HPLC. The relative mass loss of PLA is generally directly proportional to LA concentration (% conversion of PLA to LA). The percent conversion values are calculated by comparing HPLC results of treated samples with a standard curve plotted with known concentration values.

Figure 16:
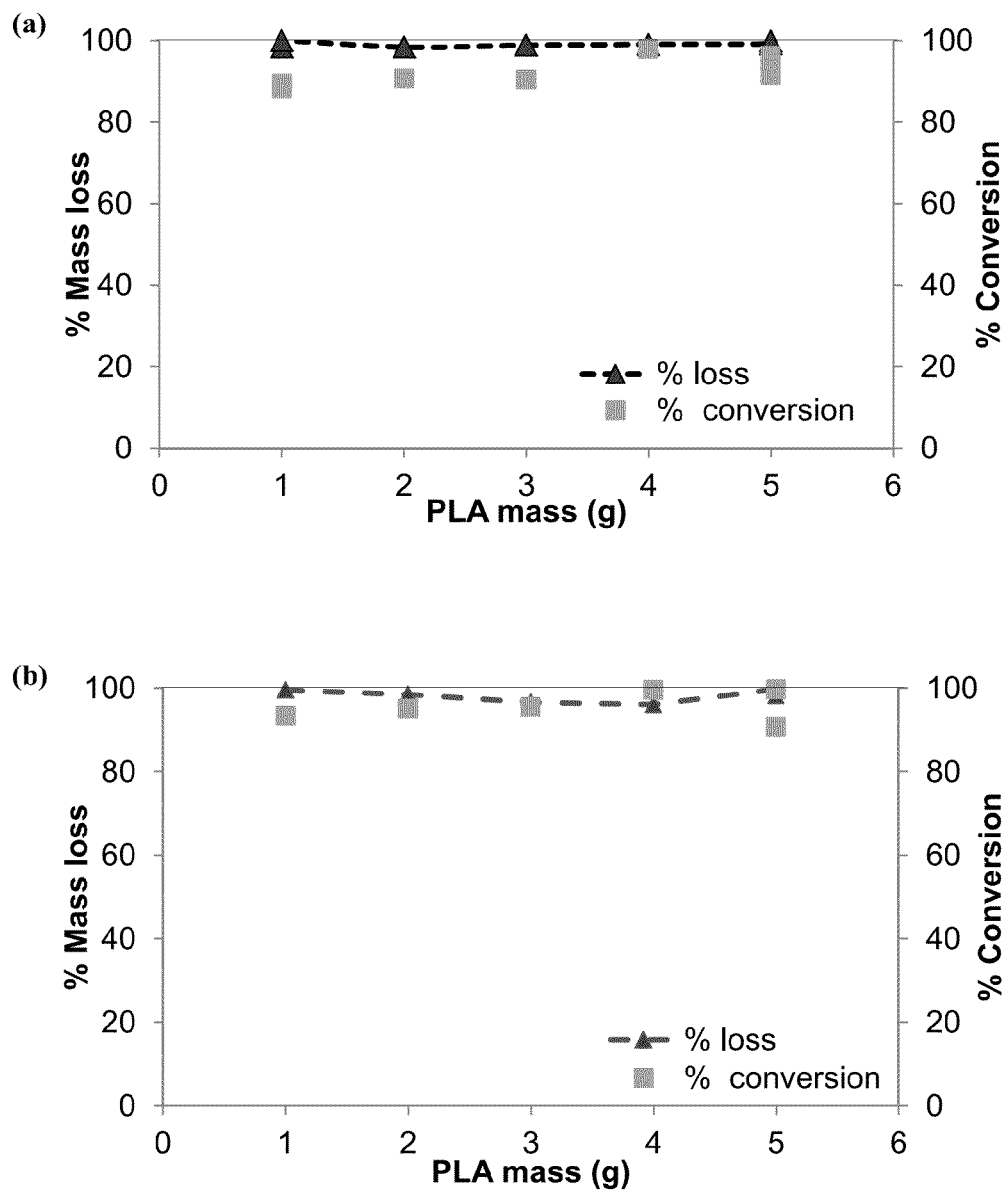
FIG. 16. Relative mass loss (%) as a function of PLA mass for MNa experiments (a) for 0.25 g sodium hydroxide and (b) 0.125 g sodium hydroxide.

Similarly, as seen in FIG. 16(a), the experiments (MNa) with 0.25 g sodium hydroxide as the catalyst depolymerized all masses of PLA (1 g to 5 g), within the reaction time of 5 min. However, with 0.125 g of NaOH, only PLA masses of 4 g or less were fully depolymerized, as seen in FIG. 16 (b), at the end of 15 min treatment time.

Figure 17:
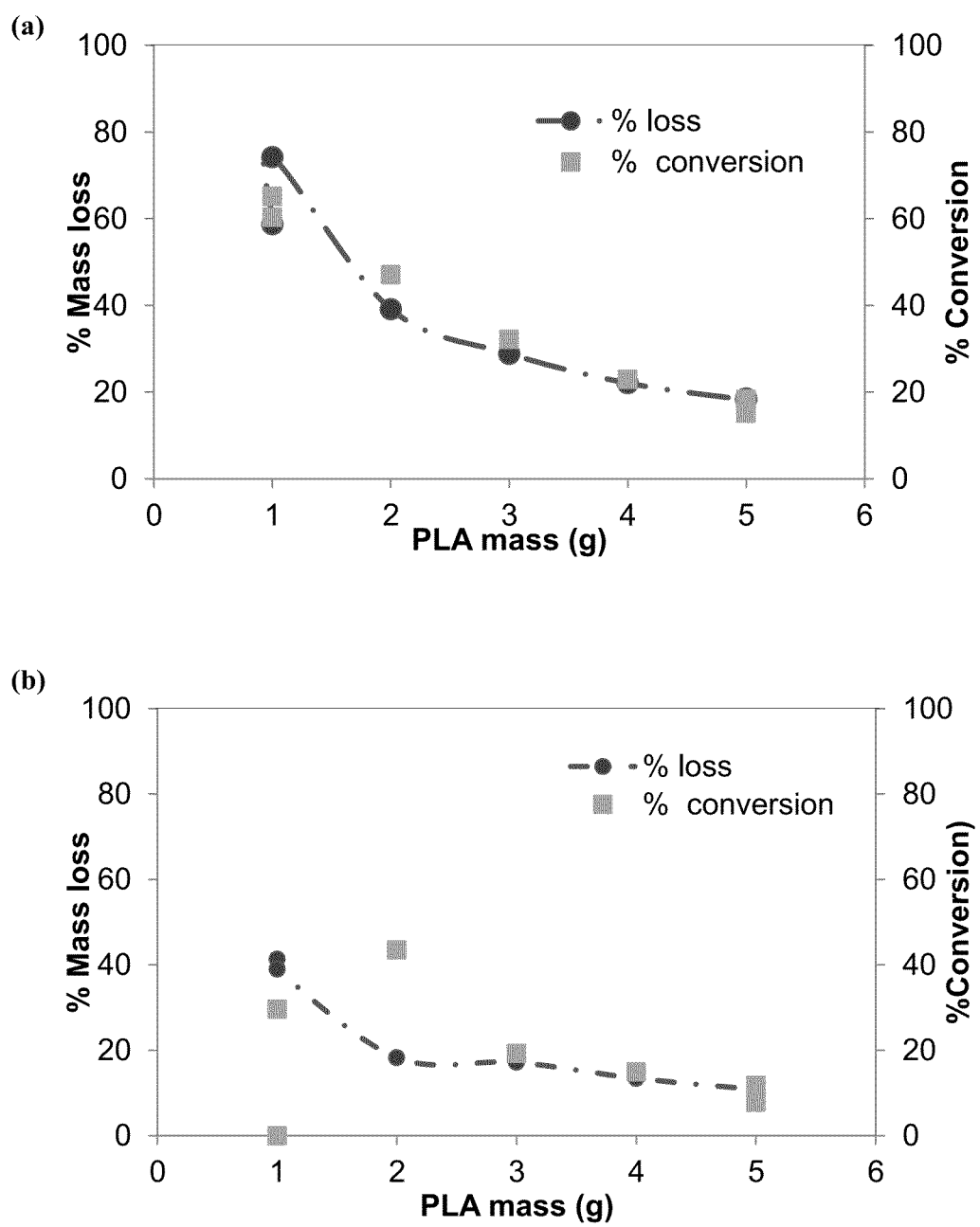
FIG. 17. Relative mass loss (%) as a function of PLA mass for ENa experiments (a) for 0.5 g sodium hydroxide and (b) 0.25 g sodium hydroxide.

In contrast with previous (MK and MNa) experiments, the results with ethanol and sodium hydroxide (ENa) resulted in a decrease in relative mass loss, with an increasing PLA sample mass independent of NaOH mass levels (0.5 g and 0.25 g), as seen in FIGS. 17(a) and (b), respectively. This indicates that these combinations of media (solvent) and catalysts are quite specific and selective in terms of effectiveness of depolymerization of PLA. There is some divergence between the HPLC and mass loss at the lower PLA mass values and it is believed that at these low concentrations, the divergence is related to experimental error.

From these results, it is concluded that depolymerization of PLA measured as relative mass loss is a dependent on the salt/catalyst mass (concentration), particularly for the combinations of potassium carbonate with methanol (MK) and sodium hydroxide with ethanol (ENa). This relationship was not seen with sodium hydroxide and methanol over the range of PLA mass that was tested here. In most figures, the data points are connected with a straight line to aid in visualization.

2.3 Results-Phase III.

Based on the results of Phase-II, a mass of 5 g of a PLA sample was selected for further optimization of the depolymerization of PLA. Results of ultrasonic experiments of MK, MNa, and ENa, discussed in Phase II, were replicated with hot bath treatment serving as the control group. The temperatures of the hot bath treatment were selected to correspond (match) the temperatures achieved during the ultrasonics treatment in Phase II. These temperatures, were dependent on the treatment medium, and were 55° C. and 65° C. for methanol and ethanol, respectively. The results of Phase III allowed the comparison of ultrasonic and hot bath treatments.

Figure 18:
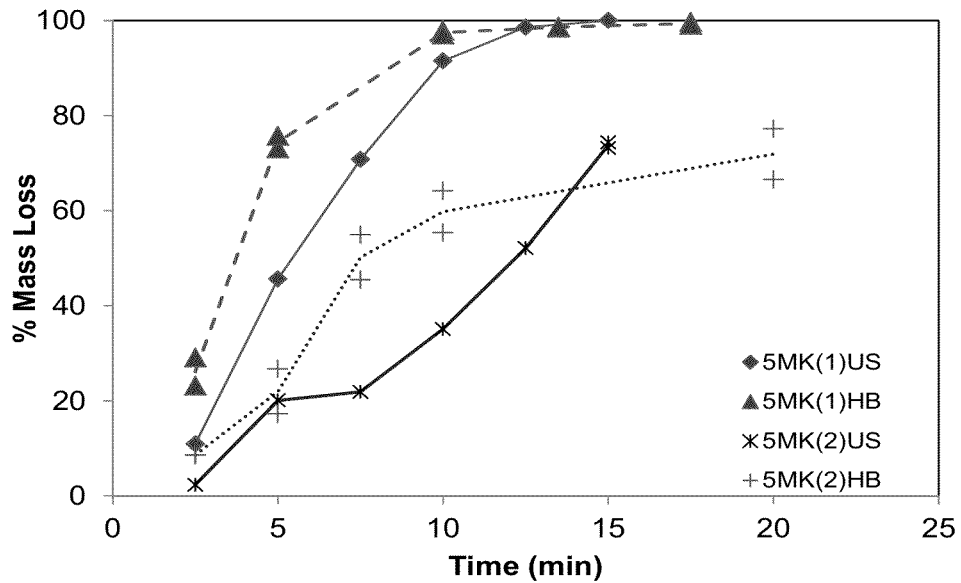
FIG. 18. Relative mass loss as a function of treatment time for MK experiments using ultrasonic (US) and hot bath (HB) treatments.

FIG. 18 shows a relative mass loss as a function of treatment time for both ultrasonics and hot bath treatments in a methanol with 0.5 g (1) and 0.25 g (2) of potassium carbonate. As expected, mass loss was generally proportional to the catalyst's mass (concentration). In addition, there is little difference between the hot bath treatment (HB) and ultrasonics (US) in terms of mass loss. Note that it is possible to fully depolymerize the 5 g of PLA in 10 min, which is much faster than reported by others (Muhammad et al., *Asian J. Chemistry* 19(3), 1714 (2006); Watanabe et al., *Macromol. Theory Simul.* 16, 619 (2007); Yagihashi et al., *Indus. Eng. Chem. Res.* 49, (2010); Motoyama et al., *Polymer Degradation and Stability*, 92(7), (2007)).

Figure 19:
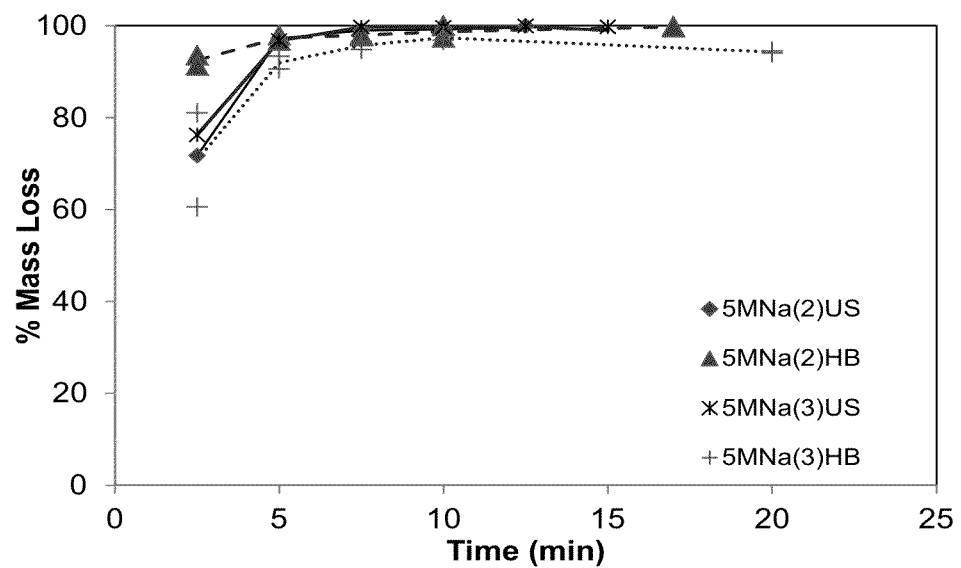
FIG. 19. Relative mass loss as a function of treatment time for MNa experiments using ultrasonic and hot bath treatments.

As shown in FIG. 19, with NaOH as catalysts, both mass levels (0.125 g and 0.25 g) resulted in 100% mass loss of PLA within 5 min for both treatments (ultrasonic and hot bath). The trends of depolymerization for both ultrasonic and hot bath treatments are very similar with the combination of methanol and sodium hydroxide at both mass levels (0.125 and 0.25 g). Again, note that this is much faster than reported by others (Muhammad et al., *Asian J. Chemistry* 19(3), 1714 (2006); Watanabe et al., *Macromol. Theory Simul.* 16, 619 (2007); Yagihashi et al., *Indus. Eng. Chem. Res.* 49, (2010); Motoyama et al., *Polymer Degradation and Stability*, 92(7), (2007)).

Figure 20:
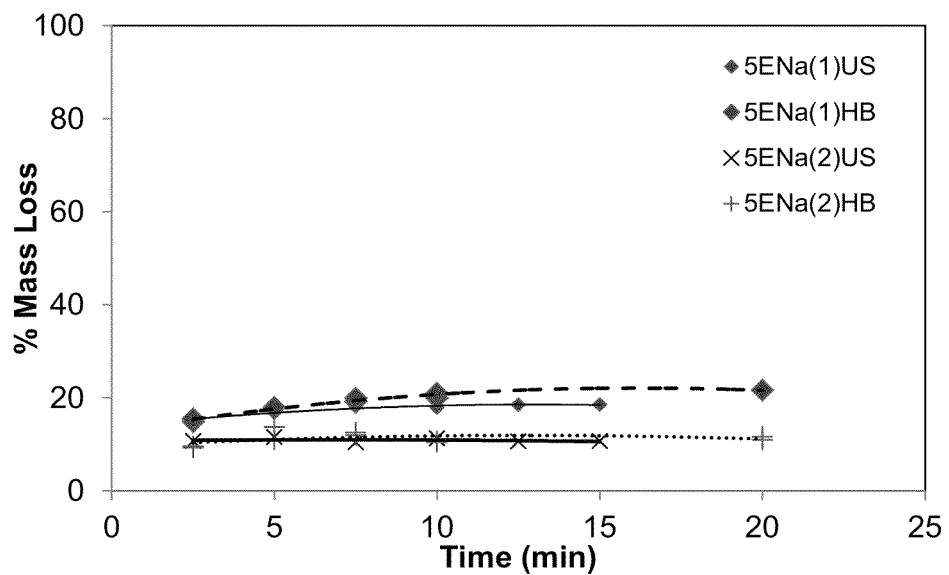
FIG. 20. Relative mass loss as a function of treatment time for ENa experiments using ultrasonic and hot bath treatments.

FIG. 20 shows that with ethanol combined with sodium hydroxide at both mass levels of 0.25 g and 0.5 g, the maximum relative mass loss was 11% and 23% respectively. The depolymerization of PLA nearly stops after 5 min of treatment. The pattern was observed for both ultrasonic and hot bat treatments. It is believed that with this combination of catalysts and media, the activity of the catalysts is inhibited by the LA and may be the result of a chemical reaction of acid (LA) and base (NaOH). There is no clear explanation why this possible effect is only seen with this combination.

Figure 21:
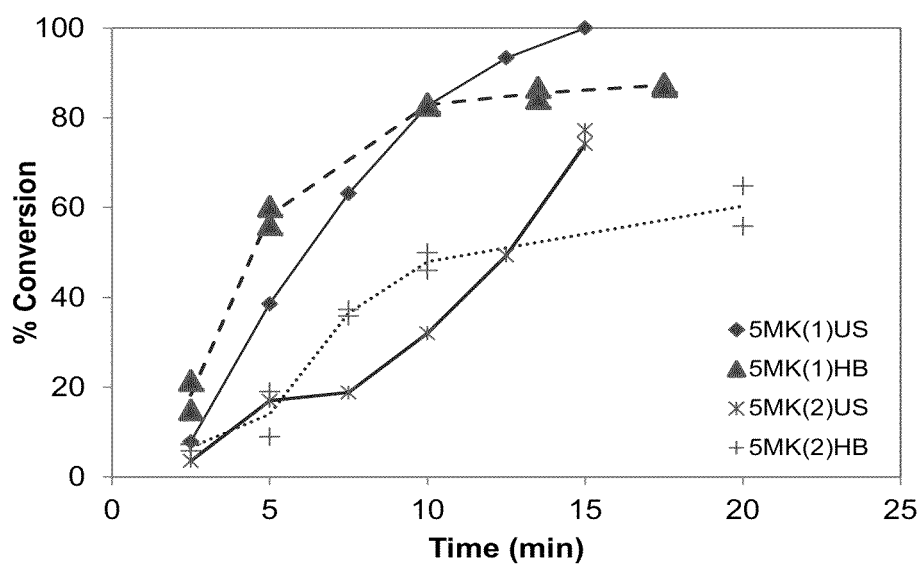
FIG. 21. Relative conversion of lactic acid (HPLC) as a function of treatment time for MK experiments using ultrasonic and hot bath treatments.
Figure 22:
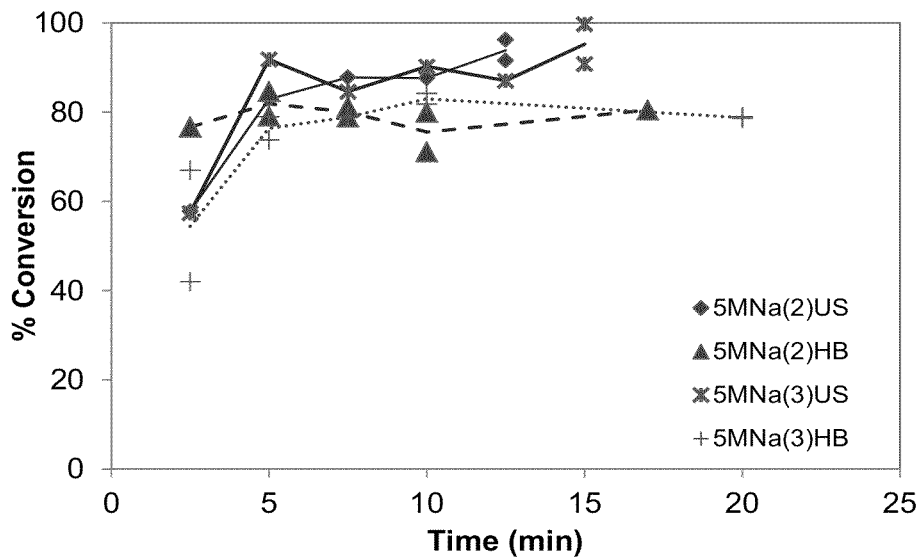
FIG. 22. Relative conversion of lactic acid (HPLC) as a function of treatment time for MNa experiments using ultrasonic and hot bath treatments.
Figure 23:
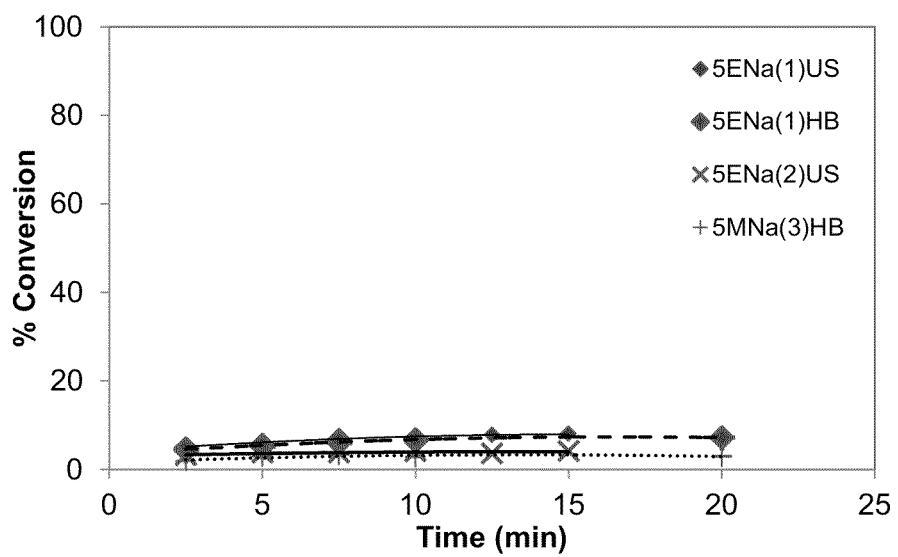
FIG. 23. Relative conversion of lactic acid (HPLC) as a function of treatment time for ENa experiments using ultrasonic and hot bath treatments.
Figure 24:
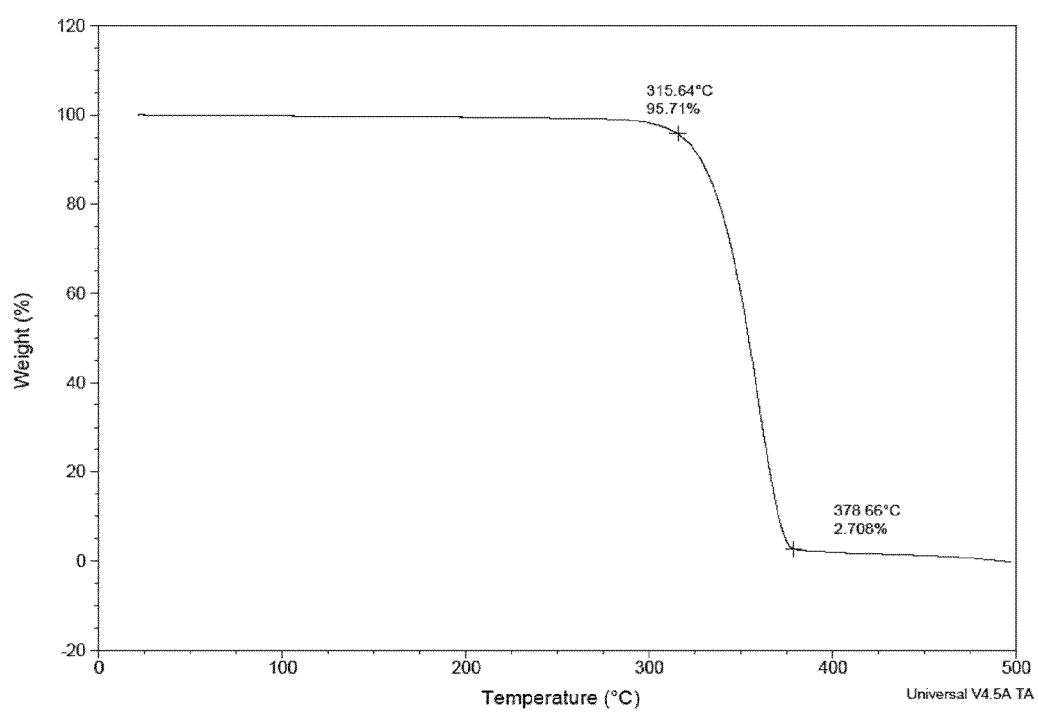
FIG. 24. Thermo gravimetric analysis of post-consumer PLA chips from water bottle.

The relative conversion of PLA into LA lactic acid as a function of treatment time are seen in FIGS. 21, 22, and 23 for methanol/potassium carbonate, methanol/sodium hydroxide, and ethanol/sodium hydroxide, respectively. The lactic acid conversion (calculated from HPLC results) as a function of treatment time exhibit results similar to relative mass loss, thereby confirming the release of lactic acid (monomer) from the PLA polymer. It is observed that relative conversion of PLA to LA is lower than 100%, unlike mass loss. This is attributed to the weight contribution by colorants and additives (2.7% w/w) in PLA as confirmed with thermal gravimetric analysis (TGA) as seen in FIG. 24, where there is approximately 2.7% residual mass. It is believed that this difference in mass loss values and relative conversion is a compound effect of additive/colorants with incomplete conversion of PLA into LA and the presence of colorants and additives. FIGS. 18 and 19 show that the relative conversion values are higher for ultrasonic treatment with respect to hot bath treatment at times near 100% mass loss. This could be because of the mixing effect caused by acoustic streaming in conjunction with cavitation effects. In general, for a majority of the experiments mass loss as a function of treatment time (min) for both ultrasonics treatment and hot bath followed a similar trend.

Figure 25:
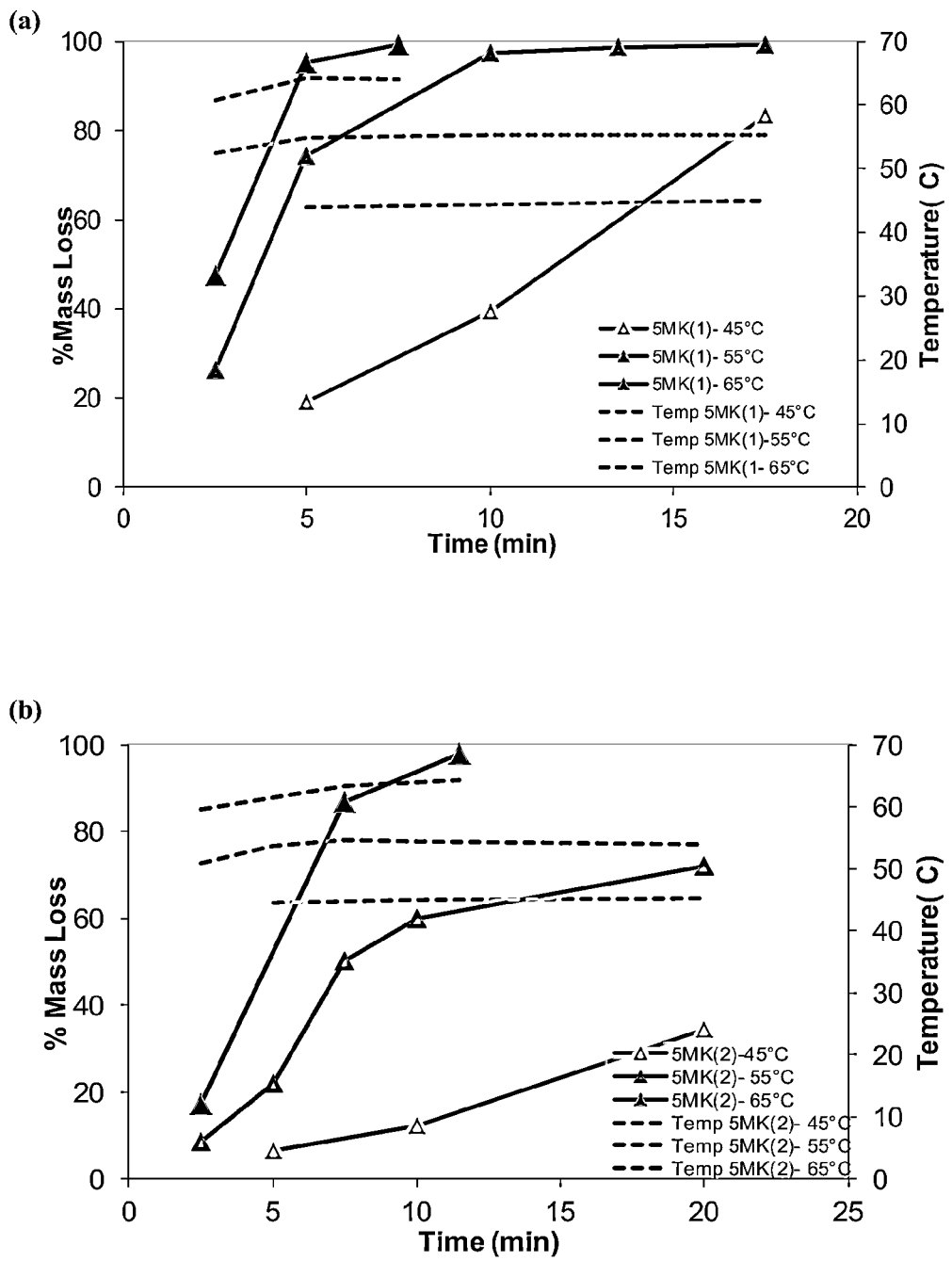
FIG. 25. Effect of treatment temperature on relative mass loss as a function of treatment time for (a) MK(1) and (b) MK(2) experiments using hot bath treatments.
Figure 26:
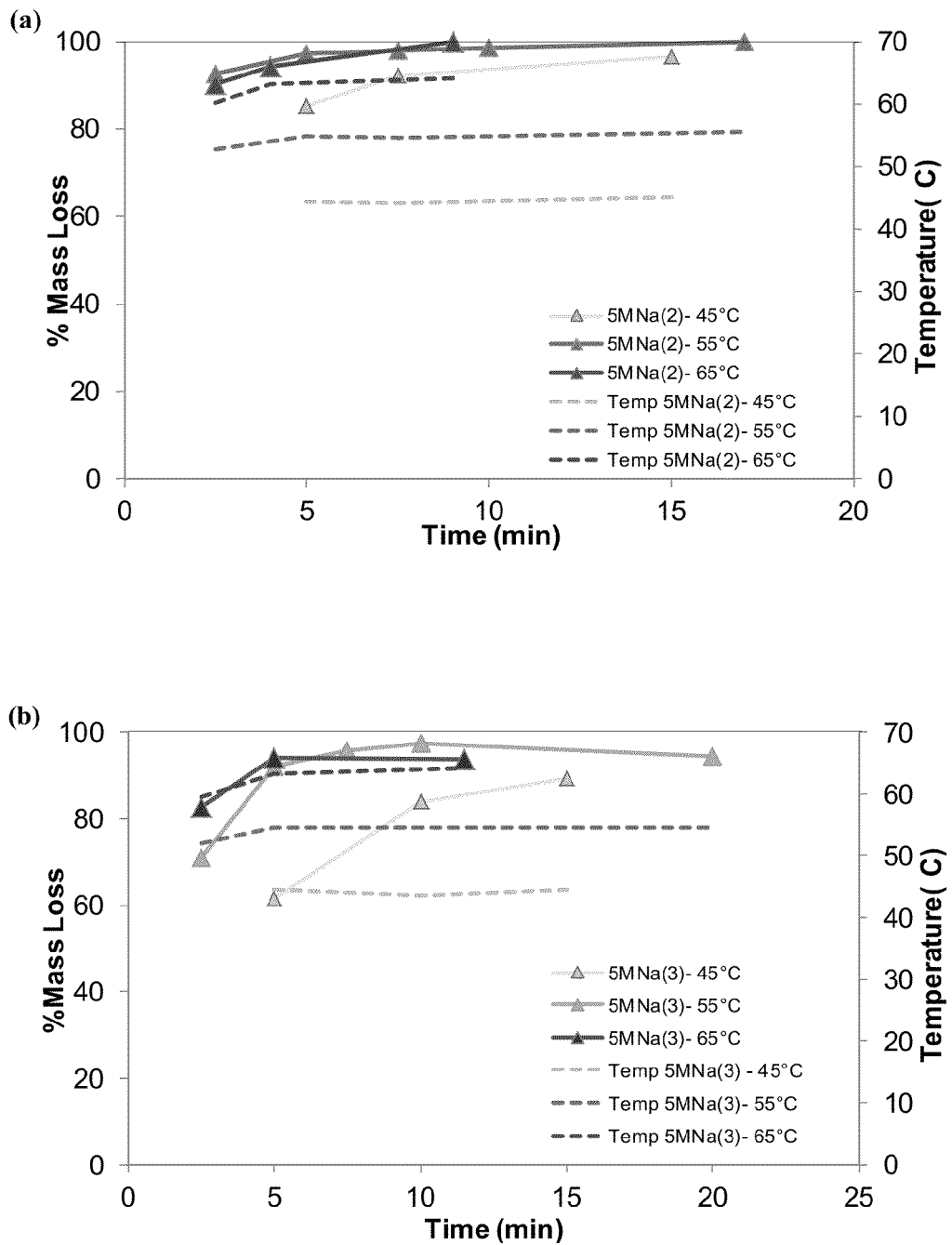
FIG. 26. Effect of treatment temperature on relative mass loss as a function of treatment time for (a) MNa(2) and (b) MNa(3) experiments using hot bath treatments.
Figure 27:
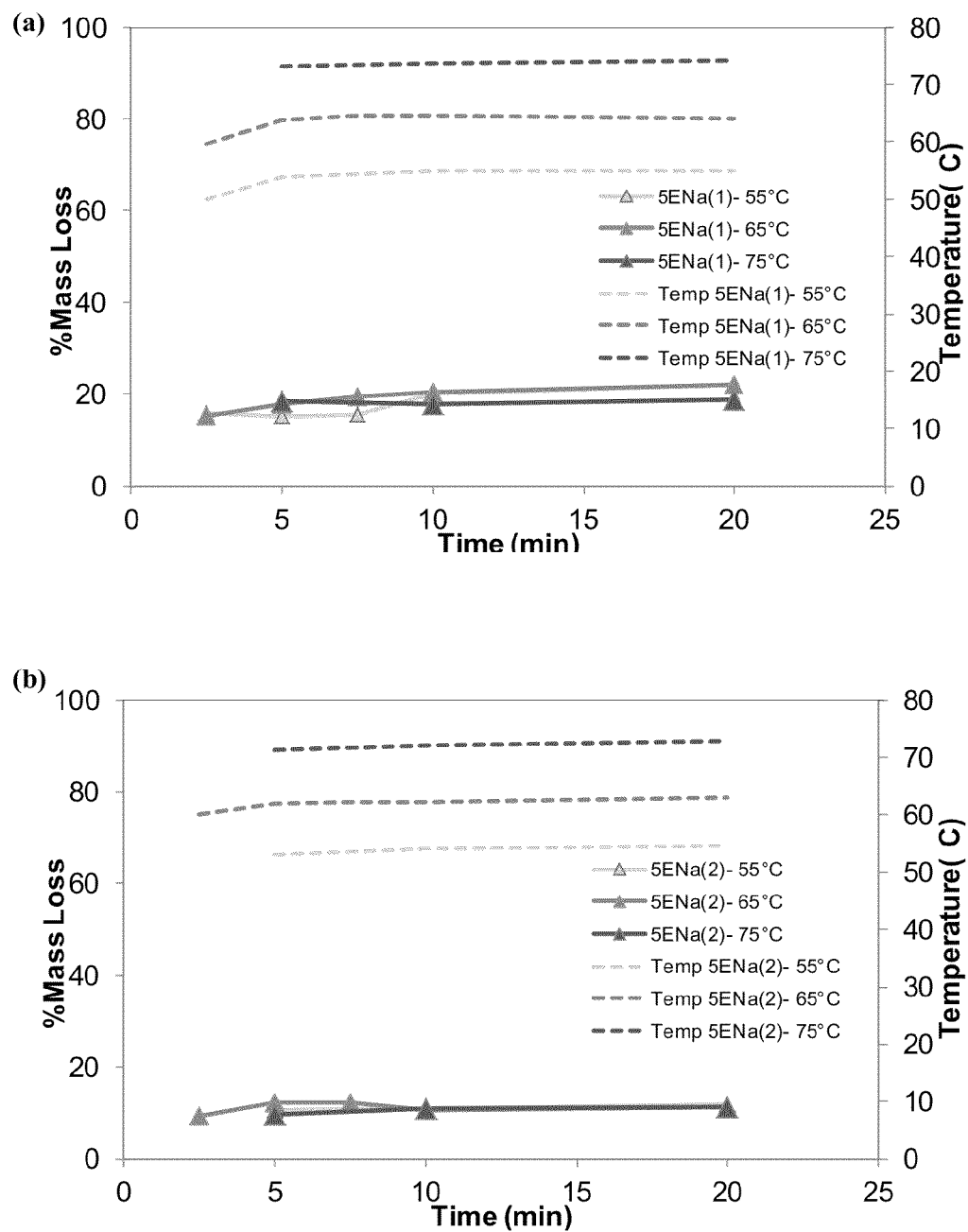
FIG. 27. Effect of treatment temperature on relative mass loss as a function of treatment time for (a) ENa(1) and (b) ENa(2) experiments using hot bath treatments.

To further optimize the depolymerization of PLA, additional studies of the effects of temperature on depolymerization (relative mass loss) of PLA were completed. This was achieved by conducting hot bath experiments at 10° C. above and below the treatment temperature observed during ultrasonic treatment to assure that the temperatures were bracketed. The relative mass losses as a function of time are shown in FIGS. 25, 26, and 27 and indicate that depolymerization of PLA is generally proportional to temperature. This relationship is more prominent with MK and MNa experiments. In these experiments, care was taken to maintain a constant temperature, but some experimental error occurred as the bath temperature typically increased slightly as a function of time. Further, lines connecting the individual points are added to aid visualization only.

2.4 Results: Scanning Electron Microscopy (SEM).

To gain insight into the impact (or lack thereof) of ultrasonic treatment, optical and scanning electron microscopy studies were completed. It was visually observed that the particle size was not significantly affected by the ultrasonic treatment. Typically, particle size is reduced by ultrasonics, particularly when particulate substrates (such as chips) are treated in a liquid ultrasonic bath. This increases the surface area to volume ratio and increases the number of reaction sites, thereby increasing reaction rates, such as depolymerization (theorized). This was not seen with the PLA chips, and it is believed to be related to the toughness of the plastic and its ability to absorb the shock waves and jets produced by ultrasonic cavitation.

FIG. 6 shows the SEM image of virgin PLA as received. The surface is relatively smooth, but becomes rough after 5 min of depolymerization treatment with sodium hydroxide (0.25 g) and methanol (0.25 g), as shown in FIGS. 7(a) with ultrasonic treatment and (b) with hot bath treatments. With ultrasonic treatment, there is a relatively rough texture on the surface, and the alignment of this texture corresponds to the stretch direction of the PLA bottle. In addition, this texture was more pronounced on the inner diameter of the bottle, where the degree of crystalline is higher because of a slower cooling. This texture is also less pronounced with the hot bath treated sample. It is believed that the ultrasonics enhanced mixing of the liquid and caused some cavitation erosion on the surface. These effects resulted in the rough surface, but the increase in the surface area was not sufficient to accelerate depolymerization.

Figure 8:
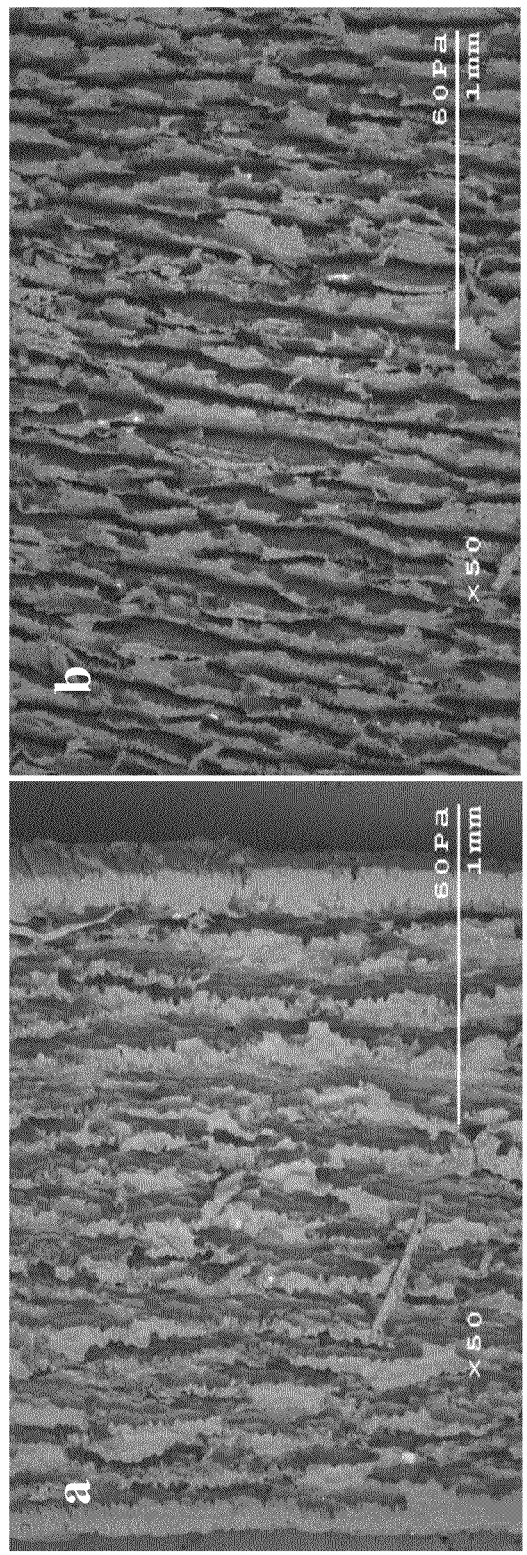
FIG. 8. Treated PLA sample at 5 minutes with $K_2CO_3$-0.5 g and methanol media (0.5 g): (a) Ultrasonics 13μ; (b) Hot bath.

A similar effect was seen with potassium carbonate (0.5 g) and methanol (0.5 g) as shown in FIG. 8, but both the hot bath (b) and the ultrasonic (a) surfaces had a similar roughness, even though the ultrasonically treated samples appear slightly rougher. Again, it is believed that the mixing effects of ultrasonics promoted surface erosion but was not sufficient to accelerate the chemical rates.

As confirmed in the next section, the laminar structure is the result of varying regions of crystallinity that are caused by the thermal history of the plastic as well as its stretching (molecular alignment) during the formation of the water bottles. That is, during the formation of the water bottles (i.e., the stretching of the bottles), the molecules are aligned in the hoop direction of the bottle. This produces regions of crystallinity with amorphous regions between them. The amorphous regions are depolymerized faster (seen as valleys), while the crystalline regions depolymerized slower (seen as peaks). This is constant with the observation that the outer diameter (faster cooling) of the PLA sheets was even less textured as a result of less crystallinity.

2.5 Confirmation of Depolymerization Selectivity: Effect of Crystallinity.

To characterize the effect of crystallinity on depolymerization, relatively crystalline and relatively amorphous samples of PLA were depolymerized under optimum conditions with the hot bath treatment. Two samples of PLA chips, each with a mass of 5 g, were prepared by heating them above the $T_g$ (75° C.) for 30 min in a platen heater to mobilize the polymers. The first 5 g samples were then quickly removed from the heater and rapidly cooled in dry ice and methanol. This rapid cooling should have prevented crystallinity and resulted in samples that were nearly 0% crystalline (~100% amorphous). The balance of the samples was then allowed to cool slowly by turning the heaters off of the platen heaters. It took approximately 120 min for the platen heater (and PLA samples) to cool to room temperature. This slow cooling should have promoted crystallinity. The balance of the samples was then depolymerized for various lengths of time to study the rate and morphology of the sample during depolymerization.

In those experiments where the effect of crystallinity on depolymerization was studied, the slowly cooled PLA samples shrank and warped, whereas the amorphous samples remained flat and unaltered. This is consistent with the fact that with more crystallinity, there is more shrinkage (less free volume). Both samples, when observed under cross-polarized light, exhibited different transmittance of light and, as expected, suggested a higher level of crystallinity with the slowly cooled sample. The birefringence patterns are indicative of a semicrystalline structure. These samples were treated with MK(1) the hot bath technique (55° C.) to observe the difference in progressive depolymerization for a cumulative time of 15 min. It was visually observed that rapidly cooled samples (amorphous) depolymerized faster when compared to slowly cooled samples, where the mass losses of these samples is higher when compared to the slowly cooled samples.

These observations indicate that the degree of crystallinity affects the rate of depolymerization, a finding that is consistent with free-volume theories. The crystalline samples have less free volume between the polymer chains, which limits the rate and depth of diffuse (penetration) of catalysts into the samples. In contrast, the amorphous samples had more free volume, thereby allowing the catalysts to penetrate into the bulk of the material. This allowed for more reaction sites and higher rates of depolymerization.

2.6 Statistical Analysis of Poly Lactic Acid (PLA) Yield Data.

The PLA yields were categorized into sets of data, each of which correlated to a particular relationship between dependent and independent variables, such as sample size (g), media/solvent type, alkali compound (catalysts), amount of alkali compound, and ultrasonic amplitude and the response variable: LA yield. For each of the smaller sets of data, one or two explanatory (independent) variables were changed while the others were maintained at a constant value.

2.6.1 Effect of Amplitude on Yield.

For a PLA sample (5 g) in methanol with 0.5 g of potassium carbonate, there were two values (two data points) of mass loss for each amplitude value (7, 13, and 19 μm (p-p)). The resulting data are detailed in Table 2-4.

TABLE 2-4

Summary of statistical data for the various ultrasonic amplitudes and effect of percentage mass loss.

| | Amplitude (μm (p-p)) | | |
|---|---|---|---|
| | 7 | 13 | 19 |
| | 72 | 100 | 100 |
| | 70 | 99 | 99 |
| Mean | 71 | 99 | 100 |
| Std. Dev. | 1.5 | 1.0 | 0.38 |

There was a statistically significant difference between the mean yields for amplitude values 7, 13, and 19 $\mu m_{p-p}$ (F=460.96, P value=0.0002). The difference between the 7 and 13 $\mu m_{p-p}$ showed a P-value near zero and a large F-factor. The 95% least significant difference (LSD) was 3.44. This means that if a difference in mean yields between two amplitudes was greater than or equal to 3.44, as seen with the 7 and 13 $\mu m_{p-p}$ and 13 and 19 $\mu m_{p-p}$, that difference was significant. The procedure has a 95% confidence level. Thus, while the amplitude did affect depolymerization yield, this effect was only seen at the lower amplitude and not at the highest amplitude, as detailed in Table 2-5.

TABLE 2-5

Tabulated summary of the statistical difference among ultrasonic amplitudes.

| Comparison (Amplitude) | Difference in means | Statistically significant? |
|---|---|---|
| 25 to 50 | 28.246 > 3.44 | Yes |
| 25 to 75 | 28.586 > 3.44 | Yes |
| 50 to 75 | 0.340 < 3.44 | No |

2.6.2 Effect of Sample Size and Amount of NaOH on Yield in Ethanol.

For samples treated in ethanol with NaOH, there were two values of yield for the four combinations of sample size (1 g and 5 g) and amount of sodium hydroxide (0.25 g and 0.50 g). This allowed for a two-factor model with interaction to be characterized by the effect of each factor individually measured.

Some combinations of sample size and amount of sodium hydroxide had a statistically significant effect on the mean LA yield. (F=40.95, P-value=0.0018). The honestly significant difference (HSD) was 22.50. The HSD is similar to the LSD and is used when making larger number of cross-comparisons. With four treatment combinations, there were 6 possible pair-wise comparisons. The HSD allows all of these values to be compared and maintain a 95% confidence. The difference in mean LA yield for the various treatment combinations, if and when greater than 22.50, correlates to a statistically significant difference.

In Table 2-6, treatment combinations sharing the same letter were not significantly different. For example 1 g, 0.50 g was significantly different than any other population, while 1 g and 0.25 g and 5 g and 0.5 g were not statistically different. In other words, the 1 g PLA sample with 0.500 g NaOH produced the highest mean yield, and this mean yield was significantly greater than the mean yields for all other combinations of size of sample and amount of NaOH.

TABLE 2-6

Tabulated data of combinations of PLA mass (1 g and 5 g) and catalysts mass (0.25 g and 0.5 g) on the statistical difference of LA yield. The statistical difference in treatment is indicated by differing alphabets (A, B, and C).

| Treatment Combination | | | | Mean Yield |
|---|---|---|---|---|
| 1 g, 0.50 g | A | | | 66.461 |
| 1 g, 0.25 g | | B | | 40.151 |
| 5 g, 0.50 g | | B | C | 18.376 |
| 5 g, 0.25 g | | | C | 10.752 |

The individual factors were also evaluated. The sample mass was statistically significant (F=98.29, P-value=0.0006) on LA yield. The 1 g mass had a statistically higher mean yield (53.3) compared to the 5 g size (14.6). Therefore, for the same amount of salt/catalyst mass, note that as the sample mass increases, the mean yield decreases significantly. The amount of NaOH was statistically significant (F=18.9, P-value=0.0122) on LA yield. The larger amount of NaOH (0.50 g) produced a significantly higher mean yield (42.4) compared to the smaller amount of NaOH (0.25 g), which had a mean yield of 25.5. Therefore, the yield was generally proportional to the amount of NaOH. The interaction between sample mass and amount of NaOH was not statistically significant (F=5.72, P-value=0.0751).

2.6.3 Effect of Sample Size and Amount of NaOH or $K_2CO_3$ on LA Yield in Methanol.

Because the amounts of $K_2CO_3$ were different from the amounts of NaOH, two separate analyses were performed: 1) Sample mass and amount of $K_2CO_3$ in methanol; and 2) Size of sample and amount of NaOH with methanol. These two are detailed below.

Sample Mass and Amount of $K_2CO_3$ in Methanol.

For samples in methanol with $K_2CO_3$ there were at least two values of yield for the four combinations of sample mass (1 g and 5 g) and amount of potassium carbonate (0.25 g and 0.50 g). This allowed a two factor model to be generated with interaction as well as the effect of each factor individually.

Some combinations of sample mass and amount of potassium carbonate had a statistically significant effect on mean yield of LA. (F=29.62, P-value=0.0013). The honestly significant difference (HSD) was 14.53.

Note that once again treatment combinations not connected by the same letter are significantly different. Table 2-7 shows that both combinations are significantly different from 1 g PLA and 0.25 g $K_2CO_3$. The 5 g PLA sample with 0.25 g $K_2CO_3$ produces the lowest mean yield, and this mean yield was significantly lower than the mean yields for all other combinations of size of sample and amount of $K_2CO_3$.

TABLE 2-7

Tabulated data of combinations of PLA mass (1 g and 5 g) and potassium carbonate catalysts mass (0.25 g and 0.5 g) on the statistical difference of LA yield. The statistical difference in treatment is indicated by differing letters (A, B, and C).

| Treatment Combination | | | Mean Yield |
|---|---|---|---|
| 1 g, 0.500 g | A | | 99.6 |
| 1 g, 0.250 g | A | | 99.5 |
| 5 g, 0.500 g | A | | 99.3 |
| 5 g, 0.250 g | | B | 73.2 |

Figure 28:
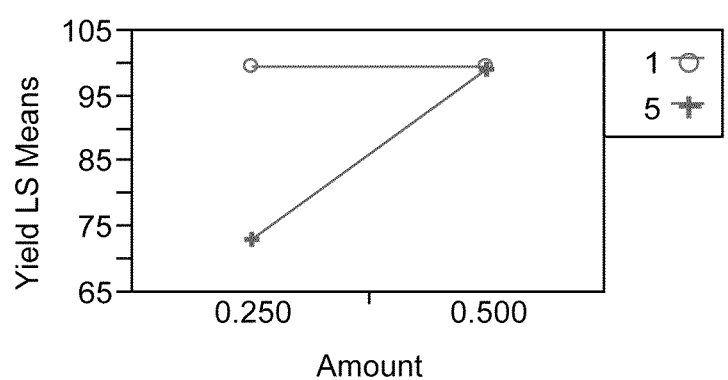
FIG. 28. Interaction plot for catalyst concentration and yield/% mass loss.

Individual factors were also evaluated. The test was statistically significant (F=24.76, P-value=0.0042). The 1 g size had a statistically higher mean yield (99.5) compared to the 5 g sample (86.3, the average of 99.3 and 73.2). Therefore, the mean yield is generally inversely proportional to sample mass. The amount of $K_2CO_3$ was statistically significant (F=24.15, P-value=0.0044). The larger amount of $K_2CO_3$ (0.50 g) produced a significantly higher mean yield (99.4) compared to the smaller amount of $K_2CO_3$ (0.25 g), which had a mean yield of 86.3. Therefore, LA yield is generally proportional to the amount of $K_2CO_3$. The interaction between sample mass and amount of $K_2CO_3$ was also statistically significant (F=23.79, P-value=0.0046). This increase in mean yield was seen when the amount of $K_2CO_3$ was increased from 0.25 g to 0.50 g. However, this increase in yield is not the same (statistically) for the various sample masses (1 g and 5 g). The interaction plot in FIG. 28 demonstrates this interaction. For 1 g samples, the amount of $K_2CO_3$ had virtually no effect on yield. However, with 5 g samples, increasing the amount of $K_2CO_3$ dramatically increases average yield.

Size of Sample and Amount of NaOH with Methanol.

For samples in methanol with NaOH, there were at least two values of yield for the four combinations with sample mass (1 g and 5 g) and amount of sodium hydroxide (0.125 g and 0.250 g). This allows a two-factor model with interactions generated by the effect of each factor individually.

None of the combinations of sample masses and amount of sodium hydroxide had a statistically significant effect on mean LA yield. (F=0.37, P-value=0.7768).

Treatment combinations not connected by the same letter are significantly different. Table 2-8 shows that all other combinations are not significantly different from each other. The individual factors can also be evaluated. The size of the sample is not statistically significant (F=0.44, P-value=0.5370). The amount of NaOH is not statistically significant (F=0.06, P-value=0.8173). The interaction between size of sample and amount of NaOH is not statistically significant (F=0.47, P-value=0.7721).

TABLE 2-8

Tabulated data of combinations of PLA mass (1 g and 5 g) and sodium hydroxide catalysts mass (0.25 g and 0.5 g) on the statistical difference of LA yield. The statistical difference in treatment is indicated by differing letters (A, B, and C).

| Treatment Combination | | Mean Yield |
|---|---|---|
| 1 g, 0.125 g | A | 98.800 |
| 1 g, 0.250 g | A | 99.467 |
| 5 g, 0.125 g | A | 98.970 |
| 5 g, 0.250 g | A | 99.570 |

2.7 Validation of Finite Element Analysis Modeling with Particle Image Velocimetry (PIV).

Figure 29:
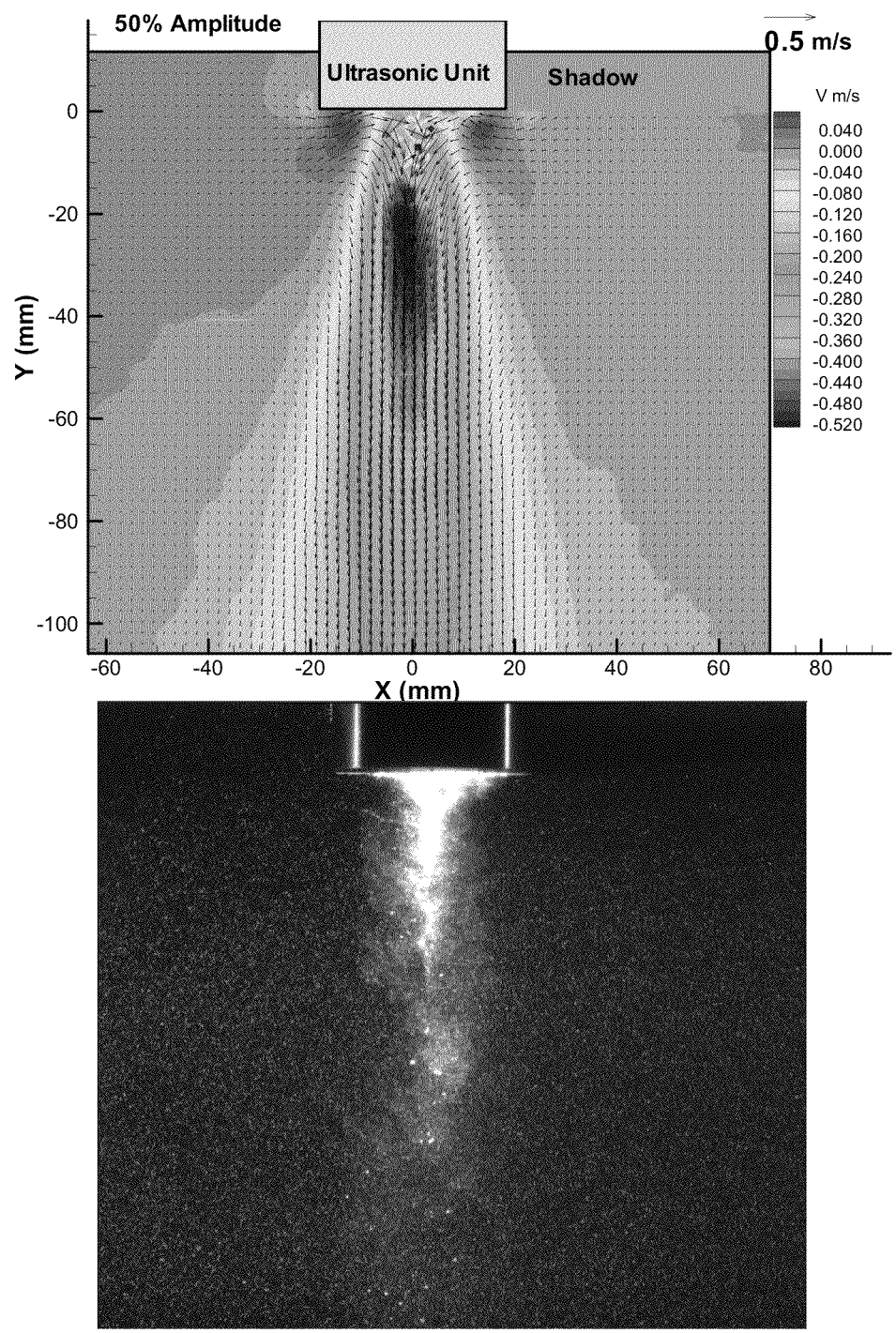
FIG. 29. Photograph of ultrasonics turbulence as capture by PIV.
Figure 30:
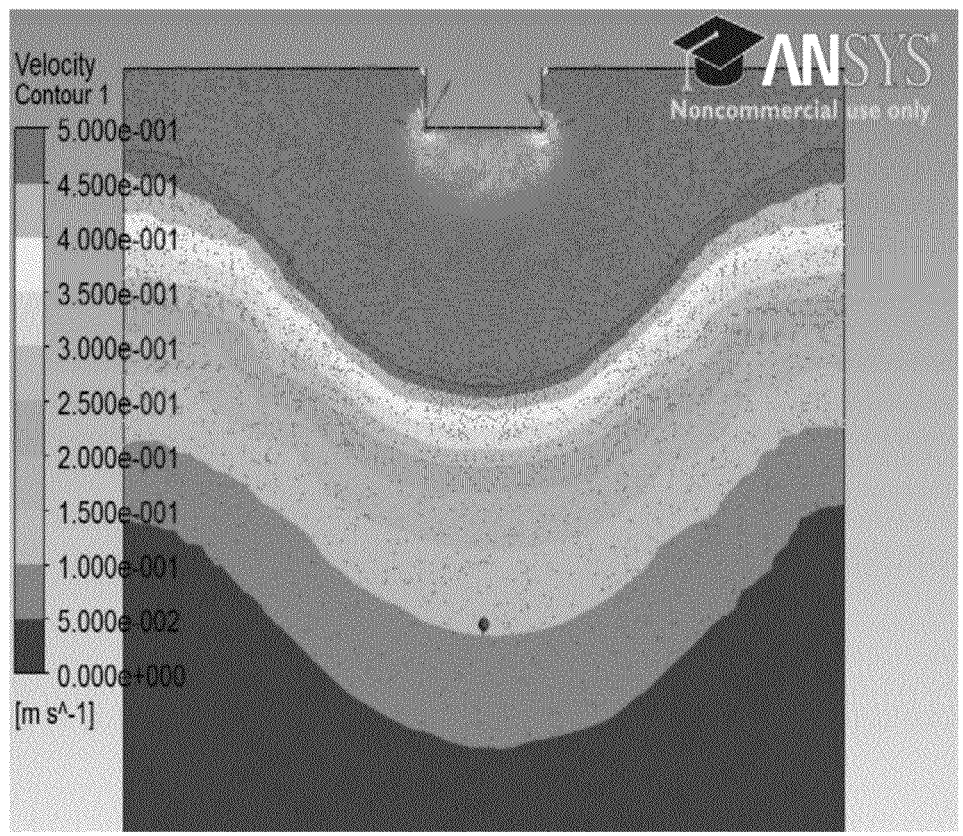
FIG. 30. Predicted velocity of water in beaker with FEA.
Figure 31:
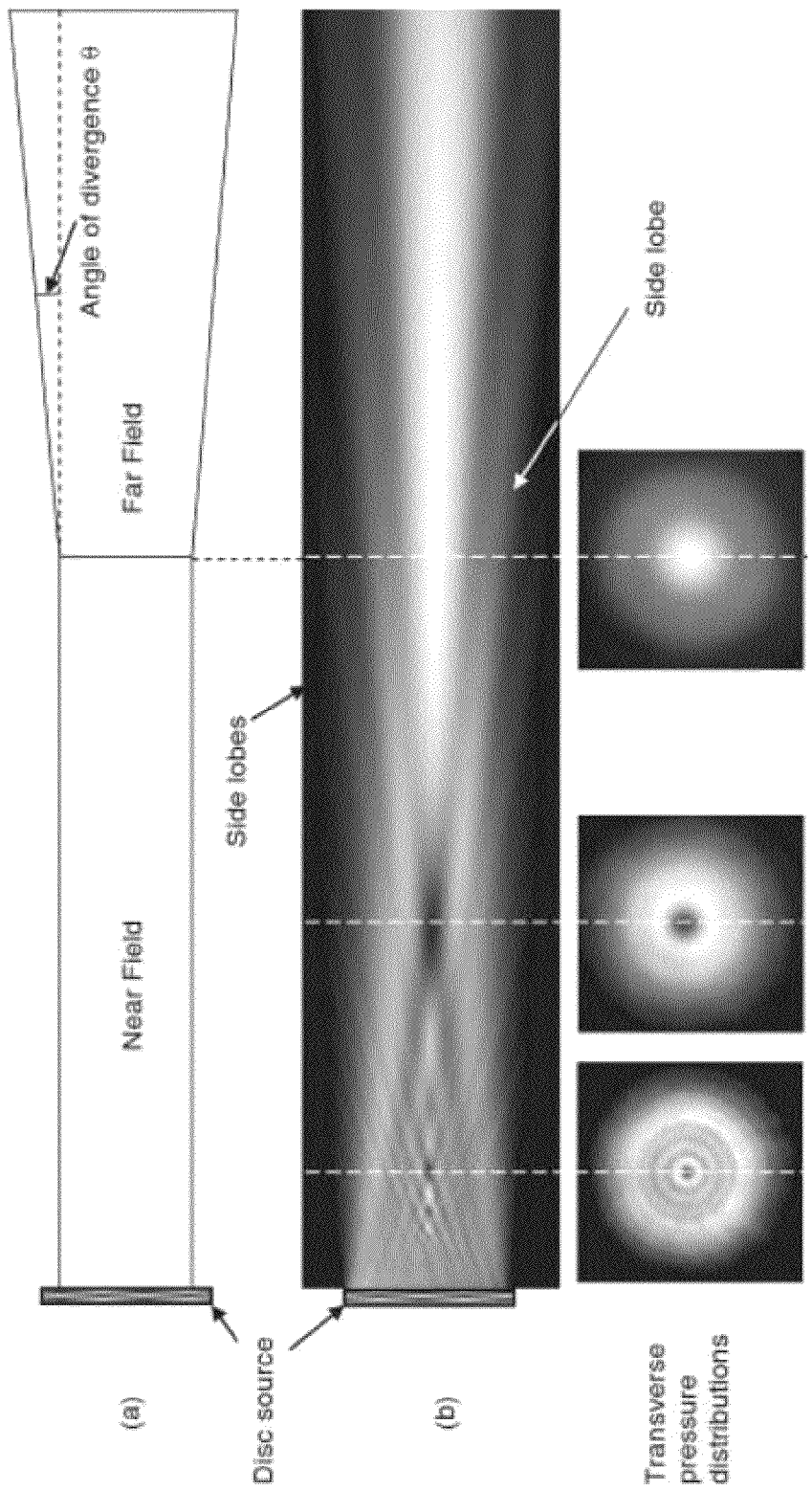
FIG. 31. Near field and far field effects of ultrasound from a planar disc source (Hoskins. P. R., Martin. K, Thrush A. Pg 16, "Diagnostic Ultrasound: Physics and Equipment" (2010)).

The FEA models were validated by comparing the predicted fields with measured velocity fields. The velocity field was measured using a laser illuminated tracking technique with natural buoyancy particles ($TiO_2$) with a diameter of 1 µm. It was assumed that the beads had insignificant inertia and that their velocity would correspond to the water velocity. The images of the illuminated particles were captured with a CCD and the sequential images processed with a proprietary software package. Based on spatial locations of the particles from frame to frame the software calculated the velocities of the particles. These velocities were then plotted as contour plots. FIG. 29 shows the contour plot and a single frame of the images recorded for the ultrasonic amplitude of 13 $\mu m_{p-p}$. These experiments were conducted for several seconds at three ultrasonic amplitudes: 7, 13, and 19 µm. FIG. 30 shows the contour plot of velocities predicted by FEA analysis.

While the maximum velocities are in agreement, the velocity fields are not. For example, in the experimental velocity fields, the maximum velocity contour map forms an inverter "cone"-shaped field below the horn. However, in the model, this maximum field has a "bowl" shape below the horn at a relatively large distance. It is believed that this is because water is assumed to be incompressible, while at the accelerations observed (~1000 g), water is compressible.

The flow patterns as observed from both PIV analysis and Ansys FEA model are in concurrence with near-field and far-field effects of ultrasound diffraction. A classical explanation of these effects for a circular disc source is as depicted in FIG. 30.

The ultrasound follows a cylindrical beam shape with the similar cross-sectional geometry as the vibration source within the near field region. It should be noted that the pressure is uniform in the near field region of the medium. The length over which near field effects prevail can be determined based on the Rayleigh distance. In the far field region, constructive and destructive interference lead to maximum intensities (toward center) and near zero intensity regions. In the far field region, the pressure difference caused by ultrasound interference results in turbulence and mixing in the medium. The Rayleigh distance for the ultrasonic source is determined from the Eq. 13 (University of South Hampton, UK, "Fundamentals of Ultrasonic wave propagation", Humphrey V (2011)) where 'a' is the radius of circular horn face (19.5 mm) and λ (74.2 mm) is the wave length of the ultrasound in a water medium (speed of sound in water $c_{water}$=1484 m/s):

$$R = \pi a^2 / \lambda \quad [\text{Eq. 13}]$$

Utilizing previously mentioned values, the distance R is calculated to be 16 mm and this is shorter than 25 mm, the average distance between the ultrasonic horn surface and bottom of the treatment beaker. The Rayleigh distance and velocity vector contour plots from PIV indicate that both near and far field effects exists during the ultrasonic treatment in the utilized treatment vessel (150 mL beaker). Further change in vessel geometry for ultrasonic treatment will alter the final effects. However, because strong mixing of the chips was visually observed, it was assumed that the PLA was uniformly treated.

2.8 Energy and Conversion Efficiency.

Polylactic acid as an alternative for petroleum plastics has a heating value of only 19 MJ/kg ("Life Cycle Inventory of Five Products Produced From Polylactide (PLA) and Petroleum-Based Resins" Technical Report; (http://www.athenas-mi.ca/projects/docs/Plastic_Products_LCA_Technical_Rpt.pdf) (visited Jun. 10, 2011); Cornelissen et al., Pg 1031, "Flash co-pyrolysis of biomass with polylactic acid. Part 1: Influence on bio-oil yield and heating value", *Fuel*, Volume 87, Issue 7, June 2008). The energy consumption for production of PLA is 82.5 MJ/kg, of which 54 MJ/kg (Vinka et al. Pg 403, "Applications of life cycle assessment to Nature-Works™ polylactide (PLA) production", *Polymer Degradation and Stability* 80 (2003)) is derived from fossil fuel and the balance is from corn and its cultivation, which considered bio-renewable energy. Considering these energy values, it can be seen that energy recovery as low as 25% can be achieved by incineration of PLA. Though composting is considered an effective route, the production of new PLA will effect further consumption of fossil energy (54 MJ/kg of PLA) and result in additional greenhouse gas (GHG) emissions.

The average amount of energy utilized per ultrasonic treatment to achieve complete depolymerization was observed to range between 1.83-2.25 MJ/kg (22-27 KJ/12 g from trials) of PLA depending on treatment parameters such as medium and catalyst concentration. In comparison, for hot bath technique the combination of methanol as treatment medium with sodium hydroxide at 0.25 g the amount of energy required for depolymerization was calculated based on adiabatic heating. In more detail, the treatment medium methanol with volume of 50 mL corresponds (40 g at a density of 0.79 g/cm³) to 1.25 Moles of methanol. The specific heat or heat capacity ($C_p$) of methanol is 79 J/(mol K). The amount of energy required to raise the temperature of the methanol medium from 25° C. to 55° C. (depolymerization temperature) can be calculated by Eq. 14, where M is the number of moles and ΔT is the change in temperature $$E_{(25-55)} = M \times C_p \times \Delta T \quad [\text{Eq. 14}]$$

From the above expression for a ΔT=55-25C=30K, the energy was determined to be 0.26 MJ/kg of PLA for effectively depolymerization (neglecting energy required to maintain constant temperature). Similar calculations for HTHP process with water as a medium ($C_p$ water=75.6 J/(mol K)) and ΔT=160-25° C. and assuming the same concentration of 12 g/50 mL (PLA/water) the energy consumption is 2.34 MJ/kg of PLA. Comparison of these energy values indicates that the newly developed hot bath process with methanol as treatment medium along with sodium hydroxide utilizes 10 fold less energy than the investigated ultrasonic treatment or the HTHP process developed by other researchers.

2.9 Conclusions.

When this research began, it was believed that the use of ultrasonics could enhance and/or accelerate the depolymerization of PLA and that ultrasonics could decrease the energy required to depolymerize (enhance) and/or reduce the time required to depolymerize PLA. However, this did not prove to be the case over the range of parameters studied. While ultrasonics resulted in surface erosion of the PLA samples (chips), the effect was less significant compared to bulk erosion/depolymerization with proper media and catalysts over the range of treatment parameters studied.

Significant finding of this work include the identification of catalysts ($K_2CO_3$ and NaOH) that can depolymerize PLA within 5 to 7 min under moderate conditions (60° C.). This is in contrast to previously reported results that required aqueous conditions, long cycle times (30 min to 24 h), as well as others that required intense conditions, including high temperatures and pressures. This reduced cycle time allows for the realization of recovery of lactic acid from postconsumer PLA products, while reducing greenhouse gas emissions (less need to process biofeedstocks). The research also showed that the depolymerization of PLA was accelerated by temperature and limited by the degree of crystallinity. Finally, it is also concluded that simple models based on fundamental principles can be used to predict acoustic streaming velocities. These models were validated with experimental values from particle tracking techniques.

It was also determined that water is not an effective media/solvent for PLA depolymerization. MgO, $CuCO_3$, $CaCO_3$, and $ZnCO_3$ are also not effective catalysts for PLA depolymerization. A mass of 0.25 g of catalysts, such as NaOH in 50 mL of methanol and 5 g of PLA, is sufficient to fully depolymerize PLA in 5 to 7 minutes. Other catalysts, such as $K_2CO_3$, require higher concentrations to fully depolymerize PLA, and require depolymerization times between only 10 and 15 min.

Additionally, the combinations of $K_2CO_3$ and NaOH with methanol respectively form a rapid depolymerizing chemistry for PLA. Alkoxide radicals generated from $K_2CO_3$ and methanol can create a highly basic pH environment leading to effective depolymerization of PLA in methanol. Alkoxide radicals, along with optimum temperatures (55° C. to 75° C. in some embodiments), were found to affect depolymerization faster at lower energy (temperature) inputs compared to previous research. These lower temperatures favor the regeneration of optically pure stereoisomer. The combination of NaOH with methanol in particular was effective because of the added presence of hydroxyl radicals in the reacting media. This ultimately leads to a further increase in basic pH and more effective depolymerization.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method to convert polylactic acid to lactic acid comprising:
    contacting solid particles of polylactic acid and an alcoholic solution, wherein the solution comprises less than about 5 wt. % water, and wherein the alcoholic solution comprises an alkali metal hydroxide, an alkali metal carbonate, or both, and methanol or ethanol, to form a first mixture; and
    maintaining the temperature of the first mixture at about 30° C. to about 90° C.;
    for a period of time sufficient to depolymerize the polylactic acid of the solid particles, thereby providing a second mixture comprising lactic acid monomers or salts thereof.

2. The method of claim 1 wherein the alcoholic solution comprises methanol.

3. The method of claim 1 wherein the alcoholic solution comprises ethanol.

4. The method of claim 1 wherein the alkali metal hydroxide is lithium hydroxide, sodium hydroxide, or potassium hydroxide.

5. The method of claim 1 wherein the alkali metal carbonate is lithium carbonate, sodium carbonate, or potassium carbonate.

6. The method of claim 1 wherein the polylactic acid depolymerizes at a rate of at least about 1 g PLA/10 minutes/0.5 g alkali metal hydroxide or carbonate.

7. The method of claim 6 wherein the temperature of the first mixture is maintained at about 55° C. to about 75° C.

8. The method claim 1 wherein the solution comprises an alkali metal hydroxide and methanol or ethanol, the temperature of the first mixture is maintained at about 50° C. to about 60° C., and the polylactic acid is converted to lactic acid at a rate of at least about 1 g PLA/10 minutes/0.5 g alkali metal hydroxide.

9. The method claim 1 wherein the solution comprises an alkali metal carbonate and methanol or ethanol, the temperature of the first mixture is maintained at about 50° C. to about 60° C., and the polylactic acid is converted to lactic acid at a rate of at least about 1 g PLA/6 minutes/0.5 g alkali metal hydroxide.

10. The method of claim 1 wherein the lactic acid or salt thereof is L-lactic acid or a salt thereof.

11. The method claim 1 wherein the solution is substantially anhydrous.

12. The method of claim 1 wherein the solution comprises less than about 2 wt. % water.

13. The method of claim 12 wherein the solution comprises less than about 1 wt. % water.

14. The method of claim 13 wherein the solution comprises less than about 0.5 wt. % water.

15. The method of claim 14 wherein the solution comprises less than about 0.25 wt. % water.

16. The method of claim 1 further comprising sonicating the solid particles of polylactic acid to enhance the rate of depolymerization of polylactic acid to lactic acid or salts thereof.

17. The method of claim 1 wherein a combination of $K_2CO_3$, NaOH, and methanol are employed.

18. The method of claim 1 further comprising removing solvent from the lactic acid monomers or salts thereof.

19. The method of claim 1 further comprising isolating lactic acid from the second reaction mixture.

20. A method to convert polylactic acid to lactic acid comprising:
    contacting solid particles of polylactic acid and an alcoholic solution, wherein the solution comprises less than about 5 wt. % water, and wherein the alcoholic solution comprises an alkali metal hydroxide, an alkali metal carbonate, or both, and ethanol, to form a first mixture; and
    maintaining the temperature of the first mixture at about 30° C. to about 90° C.;
    for a period of time sufficient to depolymerize the polylactic acid of the solid particles, thereby providing a second mixture comprising lactic acid monomers or salts thereof.

21. The method of claim 20 further comprising isolating lactic acid from the second reaction mixture.

\* \* \* \* \*